United States Patent [19]

Eggers

[11] Patent Number: 5,788,647
[45] Date of Patent: Aug. 4, 1998

[54] METHOD, SYSTEM AND APPARATUS FOR EVALUATING HEMODYNAMIC PARAMETERS

[76] Inventor: Philip E. Eggers. 5366 Reserve Dr., Dublin, Ohio 43017

[21] Appl. No.: 792,967

[22] Filed: Jan. 24, 1997

[51] Int. Cl.$^6$ .................................................. A61B 5/028
[52] U.S. Cl. ............................................ 600/526; 600/479
[58] Field of Search ............................ 600/322, 341, 600/342, 368, 478, 479, 481, 508, 526, 486

[56] References Cited

U.S. PATENT DOCUMENTS

| | | | |
|---|---|---|---|
| 4,949,724 | 8/1990 | Mahutte et al. | 600/526 |
| 5,092,339 | 3/1992 | Geddes et al. | 600/486 |
| 5,611,338 | 3/1997 | Gallup et al. | 600/505 |
| 5,647,359 | 7/1997 | Lohno et al. | 600/341 |

*Primary Examiner*—Jennifer Bahr
*Assistant Examiner*—Eric F. Winakur
*Attorney, Agent, or Firm*—Mueller and Smith, LPA

[57] ABSTRACT

Method, system, and apparatus for evaluating hemodynamic parameters and, in particular, cardiac output. A pulmonary artery catheter is described which incorporates a diffuser of gas biocompatible with the body such as oxygen at an indwelling region such that the gas may be employed to carry out a dilution technique to measure cardiac output. A mixed venous blood gas level then is measured at the pulmonary artery using a gas sensor. The preferred gas sensor employs oximetry to derive values of mixed venous oxygen saturation. An alternate embodiment utilizes an electrode/electrolyte approach as the gas sensor to carry out measurement of dissolved oxygen in mixed venous blood. The system utilizes a microprocessor driven controller to develop multiple evaluations over sequential measurement intervals and to compute a variety of hemodynamic parameters including the noted cardiac output.

41 Claims, 16 Drawing Sheets

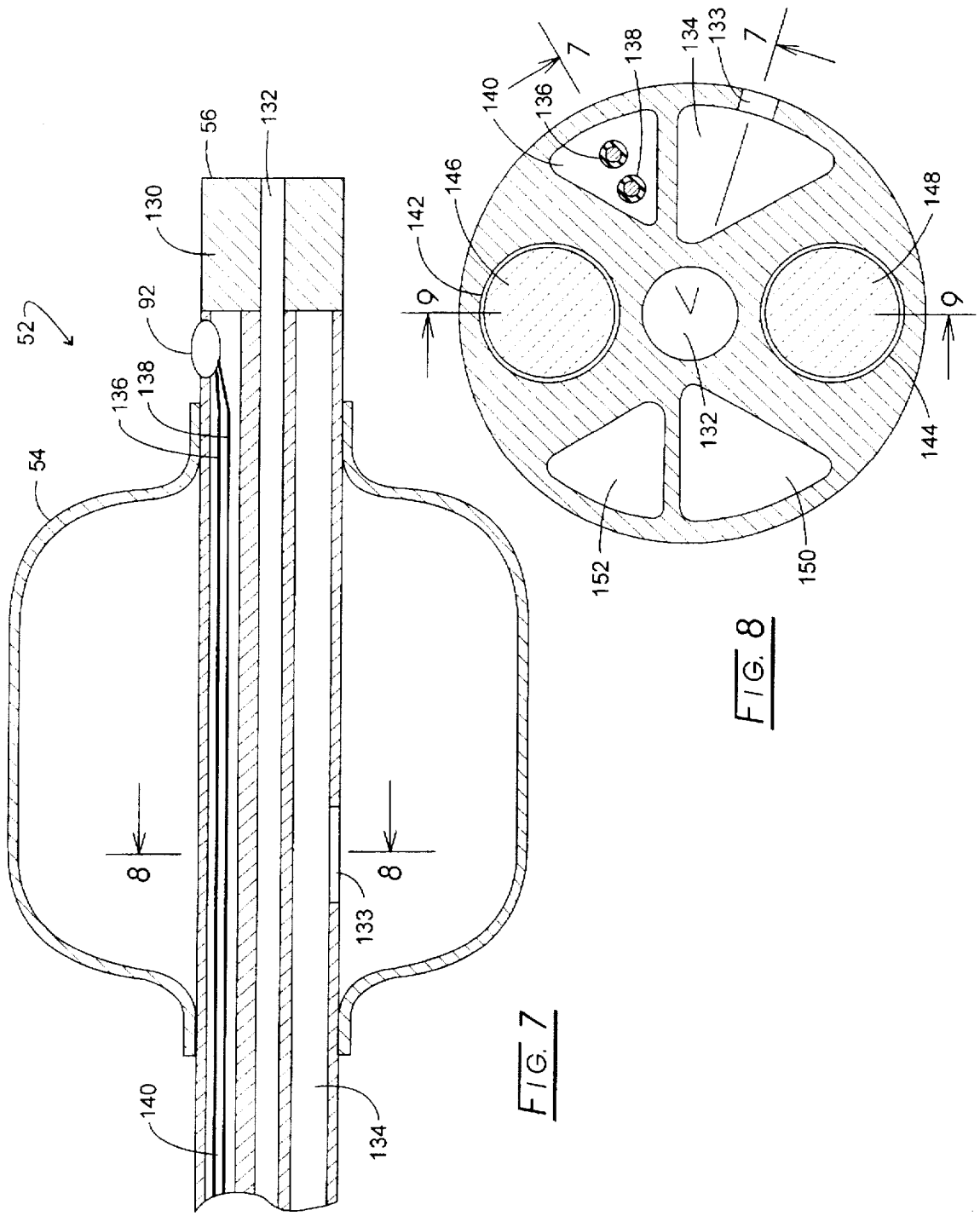

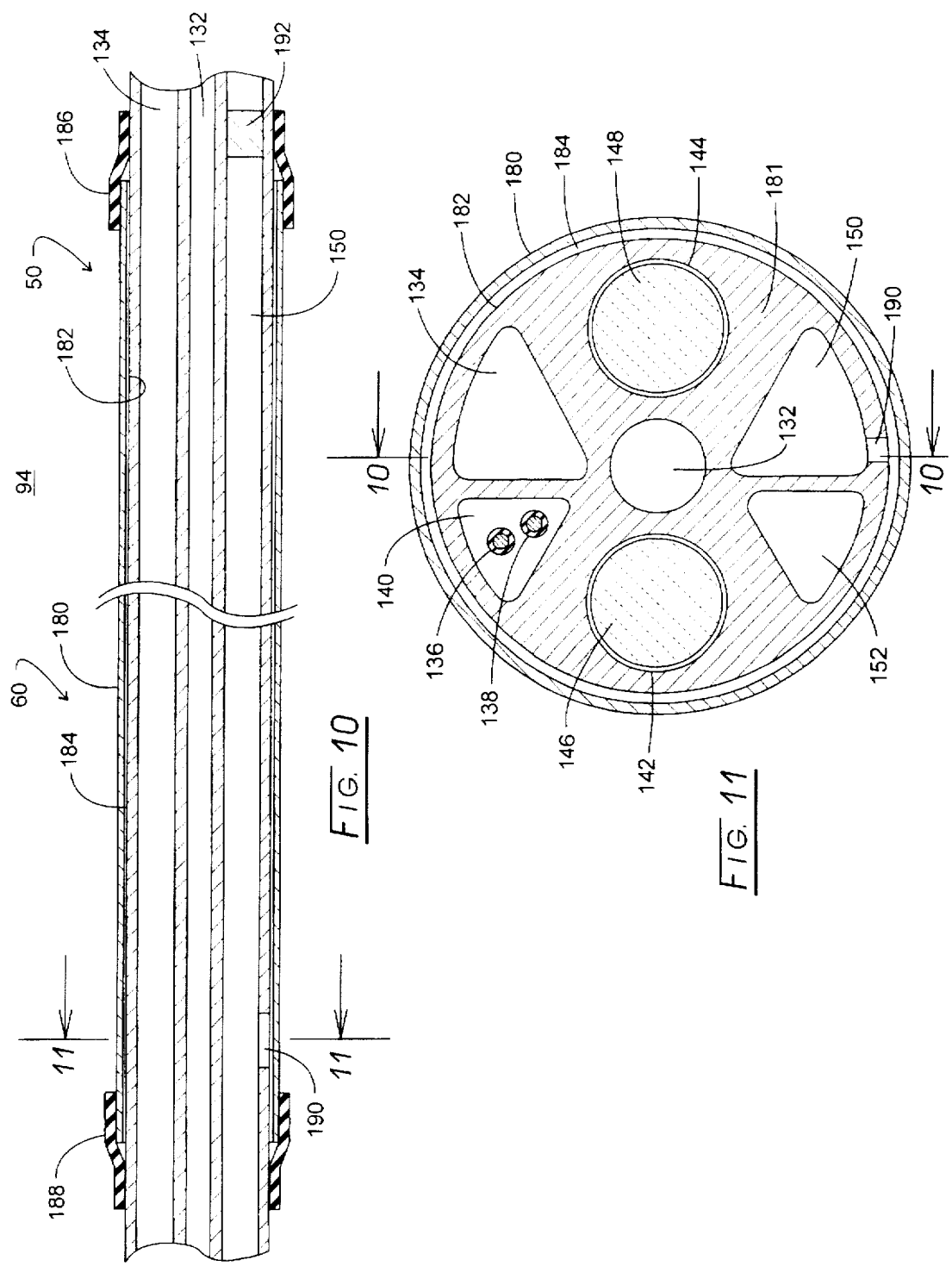

258

**DISPLAY OF
MEASURED/CALCULATED
HEMODYNAMIC PARAMETERS**

- CARDIAC OUTPUT
- CARDIAC INDEX
- PATIENT TEMPERATURE
- MIXED VENOUS OXYGEN CONTENT
- ARTERIAL OXYGEN CONTENT
- MIXED VENOUS OXYGEN SATURATION
- ARTERIAL-VENOUS OXYGEN CONTENT DIFFERENCE
- OXYGEN TRANSPORT
- OXYGEN CONSUMPTION
- OXYGEN CONSUMPTION INDEX
- SYSTEMIC VASCULAR RESISTANCE INDEX
- PULMONARY VASCULAR RESISTANCE INDEX
- STROKE INDEX
- LEFT VENTRICULAR STROKE WORK INDEX
- RIGHT VENTRICULAR STROKE WORK INDEX

FIG. 13

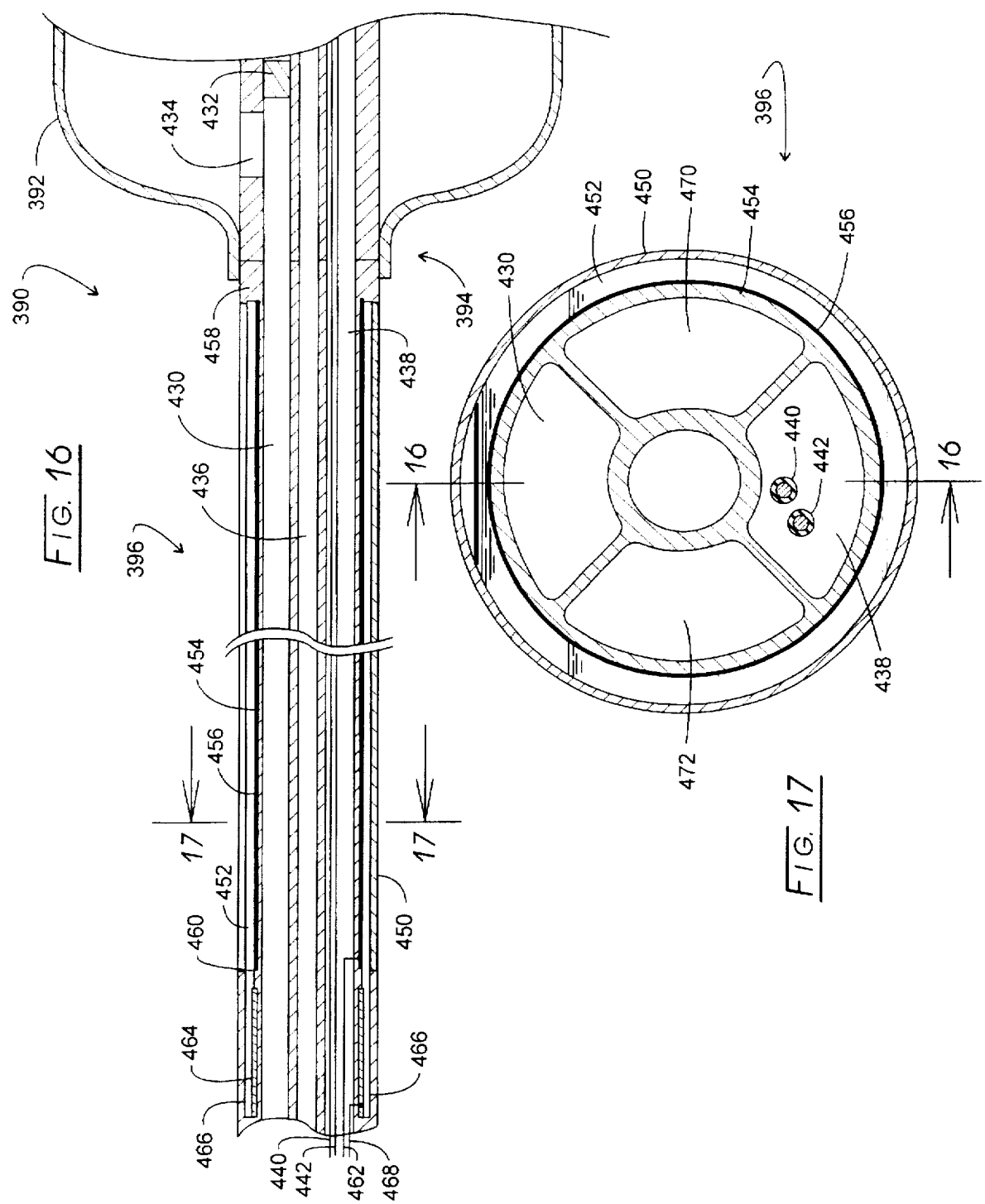

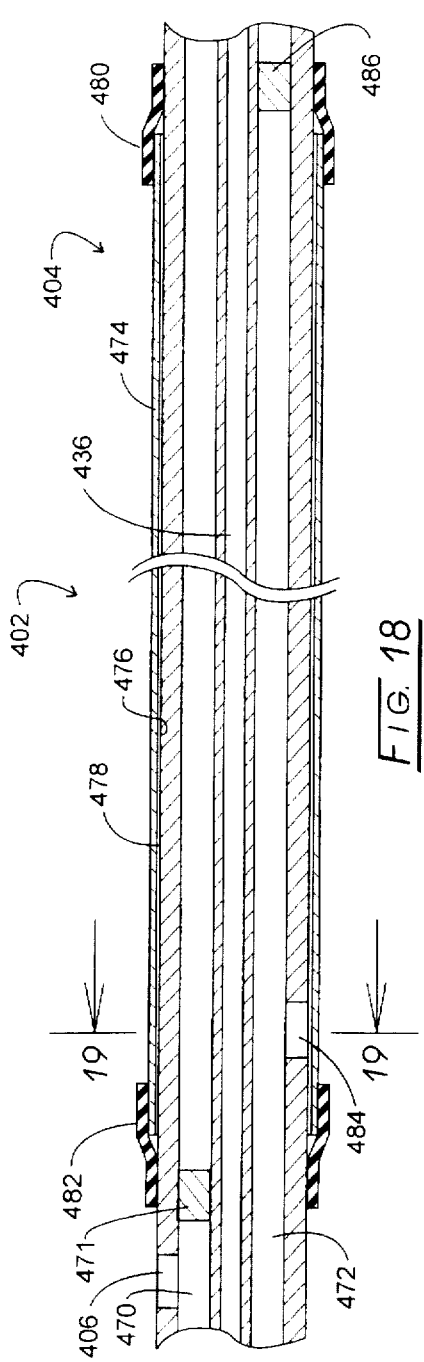
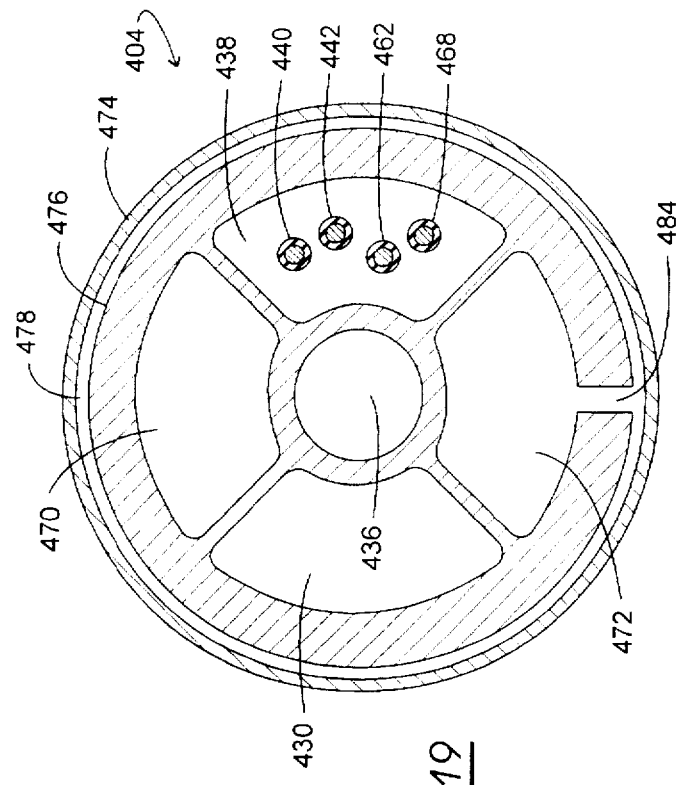

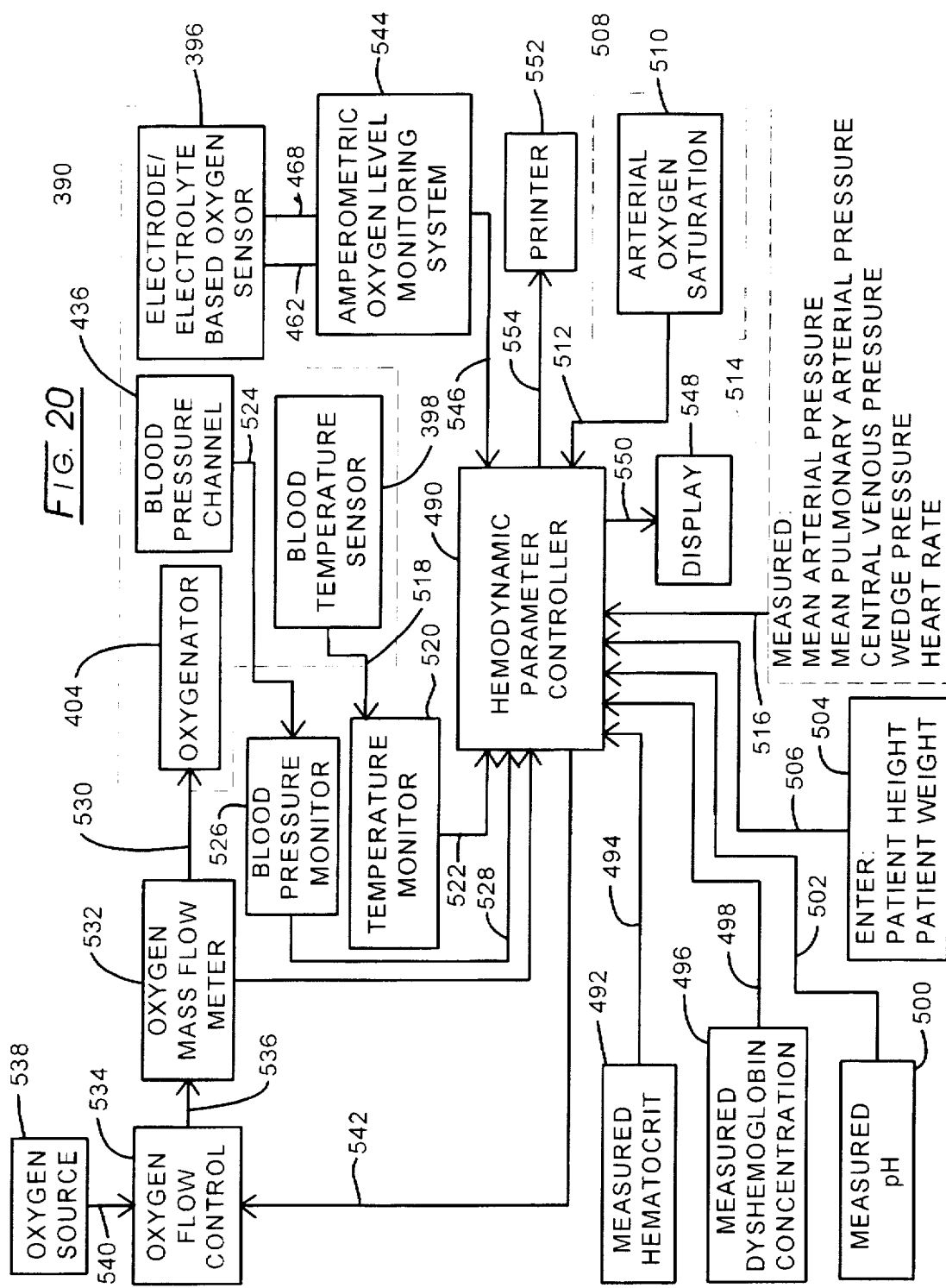

ic systems. Intensivists utilize such information along with a number of additional pulmonary factors to evaluate heart patients within intensive care units. A variety of approaches have been developed for measuring this output, all of which exhibit certain limitations and/or inaccuracies. In effect, the volumetric aspect of cardiac output provides information as to the sufficiency of oxygen delivery to the tissue or the oxygenation of such tissue. When combined with other measurements, an important evaluation of the status of the cardiovascular system of a patient may be achieved.

METHOD, SYSTEM AND APPARATUS FOR EVALUATING HEMODYNAMIC PARAMETERS

CROSS-REFERENCE TO RELATED APPLICATIONS

Not Applicable

STATEMENT REGARDING FEDERALLY SPONSORED RESEARCH

Not applicable.

BACKGROUND OF THE INVENTION

The determination of cardiac output, or measurement of the blood volumetric output of the heart is of substantial diagnostic importance for a variety of medical situations. Intensivists utilize such information along with a number of additional pulmonary factors to evaluate heart patients within intensive care units. A variety of approaches have been developed for measuring this output, all of which exhibit certain limitations and/or inaccuracies. In effect, the volumetric aspect of cardiac output provides information as to the sufficiency of oxygen delivery to the tissue or the oxygenation of such tissue. When combined with other measurements, an important evaluation of the status of the cardiovascular system of a patient may be achieved.

Currently, the more accepted approach for deriving cardiac output values is an indicator dilution techinque which takes advantage of refinements made earlier in pulmonary catheter technology. With the indicator dilution approach, a signal is inserted into the blood upstream from the pulmonary artery, and the extent of signal dilution can then be correlated with stroke volume or volumetric output of the heart. Of these indicator dilution methods, thermodilution is the present technique of choice, and in particular, that technique employing a cold liquid injectate as the signal. This approach is invasive, requiring placement of a Swan-Ganz pulmonary artery catheter such that its tip or distal end functions to position a temperature sensor just beyond the right ventricle within the pulmonary artery. The indicator employed is a bolus of cold isotonic saline which is injected from the in-dwelling catheter into or near the right atrium. Downstream blood temperature then is monitored to obtain a dilution curve relating temperature deviation to time, such curves sometimes being referred to as "wash out" curves. Combining the area under this thermodilution curve with the amount of energy subtracted by cooling of the blood provides a measure of the rate at which the heart is pumping blood, such rate usually being expressed in liters per minute. If cardiac output is high, the area under the thermodilution curve for a given applied energy, Q, will be relatively small in accordance with the well-known Stewart-Hamilton relationship. Conversely, if cardiac output is low, the area under the thermodilution curve for a given amount of applied energy, Q, will be relatively large. See in this regard:

Ganz, et al., "A New Technique for the Measurement of Cardiac Output by Thermodilution in Man", *American Journal of Cardiology*, vol. 27, April, 1971, pp 392–396.

In a typical procedure, a cold bolus of saline at ice or room temperature in an amount of about 5–10 milliliters is injected through the catheter as a measurement procedure which will require about two minutes to complete. For purposes of gaining accuracy, this procedure is repeated three or four times and, consequently, the procedure requires an elapsed time of 4–5 minutes. Thus, up to about 40 ml. of fluid is injected into the pulmonary system of the patient with each measurement which is undertaken. Accordingly, the procedure is carried out typically only one to two times per hour over a period of 24 to 72 hours. While practitioners would prefer that the information be developed with much greater frequency, the procedure, while considered to be quite accurate, will add too much fluid to the cardiovascular system if carried out too often. Of course, the accuracy of the procedure is dependant upon an accurate knowledge of the temperature, volume, and rate of injection of the liquid bolus. Liquid volume measurements are difficult to make with extreme accuracy. For example, a syringe may be used for injecting through the catheter with the result that the volume may be shown only within several percent of its actual volume. Operator error associated with volume measurement and rate of injection also may be a problem. Because the pulmonary catheters employed are somewhat lengthy (approximately 30 inches), it is difficult to know precisely the temperature of the liquid injectate at the point at which it enters the bloodstream near the distal end of that catheter. Heat exchange of the liquid dispensing device such as a syringe with the catheter, and the blood and tissue surrounding the catheter upstream of the point at which the liquid is actually released into the blood may mean that the injectate temperature also is known only to within about five percent of its actual temperature.

Another technique of thermodilution to measure cardiac output employs a pulse of temperature elevation as the indicator signal. In general, a heating coil is mounted upon the in-dwelling catheter so as to be located near the entrance of the heart. That coil is heated for an interval of about three seconds which, in turn, functions to heat the blood passing adjacent to it. As is apparent, the amount of heat which can be generated from a heater element is limited to avoid a thermocoagulation of the blood or damage to tissue in adjacency with the heater. This limits the extent of the signal which will be developed in the presence of what may be considered thermal noise within the human body. In this regard, measurement error will be a result of such noise phenomena because of the physiological blood temperature variation present in the body. Such variations are caused by respirations, coughing, and the effects of certain of the organs of the body itself. See in this regard:

Afonzo, S., et al., "Intravascular and Intracardiac Blood Temperatures in Man", *Journal of Applied Physiology*, vol. 17, pp. 706–708, 1962.

See also U.S. Pat. No. 4,595,015.

This thermal noise based difficulty is not encountered in the cold bolus technique described above, inasmuch as the caloric content of a cold bolus measurement is on the order of about 300 calories. By contrast, because of the limitations on the amount of heat which can be generated for the temperature elevation approach, only 15 or 20 calories are available for the measurement. Investigators have attempted to correct for the thermal noise problem through the utilization of filtering techniques, for example, utilizing moving averages over 10 or 12 readings. However, where such corrective filtering approaches are utilized, a sudden downturn in the hemodynamic system of a patient will not be observed by the practitioner until it may be too late. Thermodilution techniques involving the use of electrical resistance heaters are described, for example, in U.S. Pat. Nos. 3,359,974; 4,217,910; 4,240,441; and 5,435,308.

Other approaches to the elimination of an injectant in thermodilution procedures have been, for example, to introduce the thermal signal into the flowing blood by circulating a liquid within the catheter, such liquid preferably being cooler than the blood temperature. See in this regard U.S. Pat. No. 4,819,655. While, advantageously, no injectant is utilized with such procedure, the method has the disadvantage that only a limited thermal signal is available as compared with the cold bolus approach and, thus, the measurement is susceptible to error due to physiological blood temperature variations. As another example, a technique has been proposed wherein a stochastic excitation signal present as a series of thermal pulses of varying duration is asserted within the bloodstream, and the resultant output signal downstream, now present as blood temperature variation, is measured. The blood flow rate then is extracted by cross-correlating the excitation signal and measured output signal. See U.S. Pat. No. 4,507,974.

Dilution and conductivity dilution techniques, also involving injection of an auxiliary liquid such as a dye or saline solution into the blood stream are known. See in this regard, U.S. Pat. Nos. 3,269,386; 3,304,413; 3,433,935; 3,820,530; 4,572,206; and 5,092,339. A resulting dilution or conductivity dilution curve will be seen to be similar to the above-discussed thermodilution curve. Dilution and conductivity dilution procedures exhibit certain of the deficiencies discussed in connection with the injected liquid bolus based thermodilution approach, namely difficulty in precisely controlling the rate of injection and measuring the injectate volume as well as an unsuitability of the procedure for frequent or repeated use over long periods of time. Another indicator-dilution method for determining cardiac output involves the utilization of a cation, preferably lithium, which is not already present in the blood. This cation is injected as a bolus into the blood. A cation selective electrode is used to measure the resulting cation dilution curve in a manner similar to a thermodilution measurement. Cation-dilution cardiac output measurement methods share certain of the same deficiencies as discussed above for liquid-bolus based thermodilution methods. See U.S. Pat. No. 5,395,505.

Ultrasonic echocardiography has been employed for the instant purpose. With this invasive method, a plurality of microbubbles is introduced into the blood upstream of the measurement position. As described in U.S. Pat. No. 4,316,391, an ultrasonic pulse is generated from a position opposite and spaced from the region of the flowing microbubbles, for example, using an ultrasonic transducer/receiver located outside of the body. A reflective ultrasonic image, created by reflection of the ultrasonic pulse from the microbubble dispersions is measured and correlated with cardiac output, i.e. flow rate, using conventional dilution techniques. This method preferably employs microbubbles comprising gelatin membrane-encased "inert" gas such as nitrogen or carbon dioxide to perform each measurement. As a consequence, the method is not suitable for performing clinical measurements continuously or even intermittently for an extended period of time due to the accumulation of bubble membrane material that must be cleared from the blood by the body's own cleansing processes.

A derivation of cardiac output by simultaneously measuring blood velocity and vessel geometry has been described, for example, in U.S. Pat. Nos. 4,733,669 and 4,869,263. With this approach, a Doppler pulmonary artery catheter system is provided which develops instantaneous vessel diameter measurements and a mapping of instantaneous blood velocity profiles within the main pulmonary artery. From such data, an instantaneous cardiac output then is calculated. See in this regard the following publication:

"Instantaneous and Continuous Cardiac Output Obtained with a Doppler Pulmonary Artery Catheter", *Journal of the American College of Cardiology*, vol. 13, no. 6, May, 1989, pp. 1382–1392.

A similar approach has been described which involves a technique wherein a piezoelectric ultrasound transducer is placed in the trachea of a patient in proximity to the aorta or pulmonary artery. Ultrasound waves then are transmitted toward the path of flow of blood in the artery and are reflected and received. The cross-sectional size of the artery is measured, based upon the Doppler frequency difference between the transmitted and received waves. Imaging techniques such as X-ray or radioisotopic methods also have been used. See generally the following publication:

"Transtracheal Doppler: A New Procedure for Continuous Cardiac Output Measurement", *Anesthesiology*, vol. 70, no. 1, January 1989, pp. 134–138.

See additionally, U.S. Pat. Nos. 4,671,295 and 4,722,347.

A pulse contour technique for measuring blood velocity which requires a secondary calibration is described in the following publication:

"Continuous Cardiac Output Monitoring During Cardiac Surgery", *Update in Intensive Care and Emergency Medicine,* .Berlin: Springer-Verlag, 1990, pp. 413–417.

Another approach employs a so-called "hot wire" anemometer or heated thermistor as described in U.S. Pat. No. 4,841,981; EP 235811; U.S. Pat. No. 4,685,470, and WO8806426.

Any of the velocity-based measurement techniques for deriving cardiac output confront a rather basic difficulty not present with indicator dilution approaches. That difficulty resides in the necessity for knowing the geometric cross-section of the vessel through which blood is flowing. In this regard, the geometry and diametric extent of the pulmonary artery is not known and is a dynamic, changing with the pulsation nature of blood flow. Of course, the velocity measurements themselves must account for the surface effect of the interior of the vessel, velocity varying from essentially a zero value at the interior surface or lumen of the vessel to a maximum value towards the interior of that vessel.

A non-invasive technique evaluating thoracic electrical bioimpedance to derive cardiac outputs has been studied, for example, using electrocardiographic signals (ECG). However, cross-correlations of the results with the well accepted thermodilution technique have led to questions of reliability.

For a general discourse looking to alternatives to the current indicator dilution method of choice, reference is made to the following publication:

"Alternatives to Swan-Ganz Cardiac Output Monitoring" by Moore, et al., *Surgical Clincis of North America*, vol. 71, no. 4, August 1991, pp. 699–721.

BRIEF SUMMARY OF THE INVENTION

The present invention is addressed to a method, system, and apparatus for evaluating the hemodynamic state of the cardiovascular system of the body of a patient. Using a specially reconfigured pulmonary artery catheter, the new technique employs a gas which is biocompatible to the body of the patient as the injectant in the course of carrying out cardiac output analysis with a dilution technique. By sensing a mixed venous blood gas level at the pulmonary artery, cardiac output as well as a variety of related hemodynamic parameters may be measured and computed. Advantageously, the cardiac output evaluation procedure may be carried out more repetitiously over extended periods of time. Thus, the technique may be administered and attendant hemodynamic parameter data developed using a microprocessor driven controller, performing in conjunction with dynamic and chart-form displays capable of giving the intensivist immediate and timeline based information.

A preferred biocompatible gas for use with the method is oxygen, a selection serving to enhance the available number of measurements and computed hemodynamic parameters. A Swan-Ganz type pulmonary artery catheter is employed with the procedure which is configured having a gas diffuser such as an oxygenator spaced inwardly from its distal end at an indwelling region. That region is selected such that oxygen is diffused into the bloodstream near the entrance to and/or within the right atrium of the heart. The distal end of the catheter is configured in conventional fashion with an inflatable/deflatable balloon serving the conventional purpose of positioning the catheter tip within pulmonary artery and being periodically inflatable to measure wedge pressure. Located at this distal end or tip portion is a gas sensor which is an oxygen sensing arrangement in the preferred embodiment. Further, the tip preferably will contain a pressure monitoring channel or lumen and a temperature monitoring device such as a thermistor. With the procedure, blood oxygen levels of mixed venous blood within the pulmonary artery initially are measured to develop a baseline value thereof. Then, oxygen is diffused into the blood at the vicinity of the right atrium at a controlled mass rate and mixed venous blood oxygen level again is monitored to develop cardiac output based hemodynamic parameter information to achieve a measurement of cardiac output by dilution technique. Because there is no sensitivity to naturally occurring alterations of blood temperature, nor is there an addition of fluids to the blood supply, the procedure may be carried out more repetitiously over extended intervals of time.

Two approaches to measuring mixed venous blood oxygen levels are described, the preferred approach utilizing reflectance oximetry. This approach may be implemented by incorporating light transmission and light reflectance fiber optic bundles within the pulmonary artery catheter which extend from its proximal end to its distal tip, the procedure preferably being carried out using three or more wavelengths of light to measure the level of bound oxygen by measuring the reflectance levels from two species of hemoglobin.

In another approach, dissolved oxygen in mixed venous plasma is measured utilizing an electrode/electrolyte-based oxygen sensor such as a Clark electrode in conjunction with an amperometric oxygen level monitoring system. With this arrangement, two electrodes are mounted at the distal region of the pulmonary artery catheter which are immersed behind a membrane within an electrolyte. Dissolved mixed venous blood oxygen will be represented by a current evoked between the two electrodes when they are held at a minor voltage difference.

A further feature of the invention is to provide apparatus for evaluating the hemodynamic state of the cardiovascular system of the body of a patient. A pulmonary artery cathether is provided having a distal end which is positionable within mixed venous blood at the pulmonary artery of the body and an indwelling region spaced rearwardly therefrom, the catheter extending to a proximal end. A diffusion channel is provided within the catheter having a gas input connectable with a controlled source of gas biocompatible with the body and extending to an infusion component located at the indwelling region and configured for infusing the gas into the bloodstream of the body. A gas sensor component then is mounted upon the catheter at the distal end and has an output which corresponds with the level of the biocompatible gas within the pulmonary artery.

The invention further features a method for evaluating the hemodynamic state of the cardiovascular system of the body of a patient which comprises the steps of:

(a) providing a pulmonary artery cathether having a proximal end, a distal end, and an indwelling region spaced rearwardly therefrom, a diffusion channel within the catheter having a gas input connectable with a source of gas biocompatible with the body and extending to an infusion component located at the indwelling region and configured for infusably conveying the gas into the bloodstream of the body, and a gas sensor component mounted upon the catheter at its distal end and having an output corresponding with a level of the biocompatible gas within blood at the location of the sensor, (b) positioning the pulmonary artery catheter within the bloodstream of the body, locating the sensor component at the pulmonary artery, and the infusion component upstream therefrom;

(c) deriving an output from the gas sensor to provide a baseline value corresponding with a level of the biocompatible gas within mixed venous blood;

(d) then delivering the gas from the source into the diffusion channel at a predetermined mass flow rate;

(e) deriving the output from the gas sensor; and (f) deriving a value for the cardiac output of the heart of the body by correlating the baseline value, the predetermined mass flow rate, and the output derived in step (e).

Another object of the invention is to provide a system for evaluating the hemodynamic state of the cardiovascular system of the body of a patient which comprises a source of gas biocompatible with the body. A gas flow control apparatus is coupled with the source of gas and is controllable to provide a select mass flow rate of the gas at a gas output. A pulmonary artery catheter having a distal end positioned within mixed venous blood at the pulmonary artery of the body and an indwelling region located rearwardly therefrom is provided, such catheter extending to a proximal end. A blood gas level sensor component is mounted with the catheter at its distal end and is controllable to provide a sensor output at the proximal end corresponding with a blood gas level within the mixed venous blood and pulmonary artery. A diffusion channel within the catheter having an input adjacent the proximal end connected in gas flow communication with the gas output and having an infusion component located at the indwelling region for diffusing the gas with blood flowing adjacent thereto is provided. A controller is provided for controlling the gas flow control apparatus and the gas level sensor, and is responsive to the sensor output for deriving an output signal in correspondence therewith representing a value of cardiac output. A display is provided which is responsive to that output signal for displaying the value of cardiac output.

Other objects of the invention will, in part, be obvious and will, in part, appear hereinafter. The invention, accordingly, comprises the method, system, and apparatus possessing the construction, combination of elements, arrangement of parts, and steps which are exemplified in the following detailed description.

For a fuller understanding of the nature and objects of the invention, reference should be made to the following detailed description taken in connection with the accompanying drawings.

BRIEF DESCRIPTION OF THE DRAWINGS

FIG. 7 is a partial sectional and developed view taken along the wedge-shaped planes 7—7 in FIG. 8;

FIG 8 is a sectional view taken through the plane 8—8 in FIG. 7;

FIG. 10 is a sectional view taken through the plane 10—10 shown in FIG. 11;

FIG. 11 is a sectional view taken through the plane 11—11 in FIG. 10;

FIG. 13 is a view of the display and associated parameters shown in FIG. 12;

FIG. 16 is a partial sectional view taken through the plane 16—16 in FIG. 17;

FIG. 17 is a sectional view taken through the plane 17—17 in FIG. 16;

FIG. 18 is a partial sectional view taken through the plane 18—18 in FIG. 19;

FIG. 19 is a sectional view taken through the plane 19—19 in FIG. 18; and

FIG. 20 is a block diagram of the system employed with the pulmonary artery catheter of FIG. 15.

DETAILED DESCRIPTION OF THE INVENTION

Figure 1:
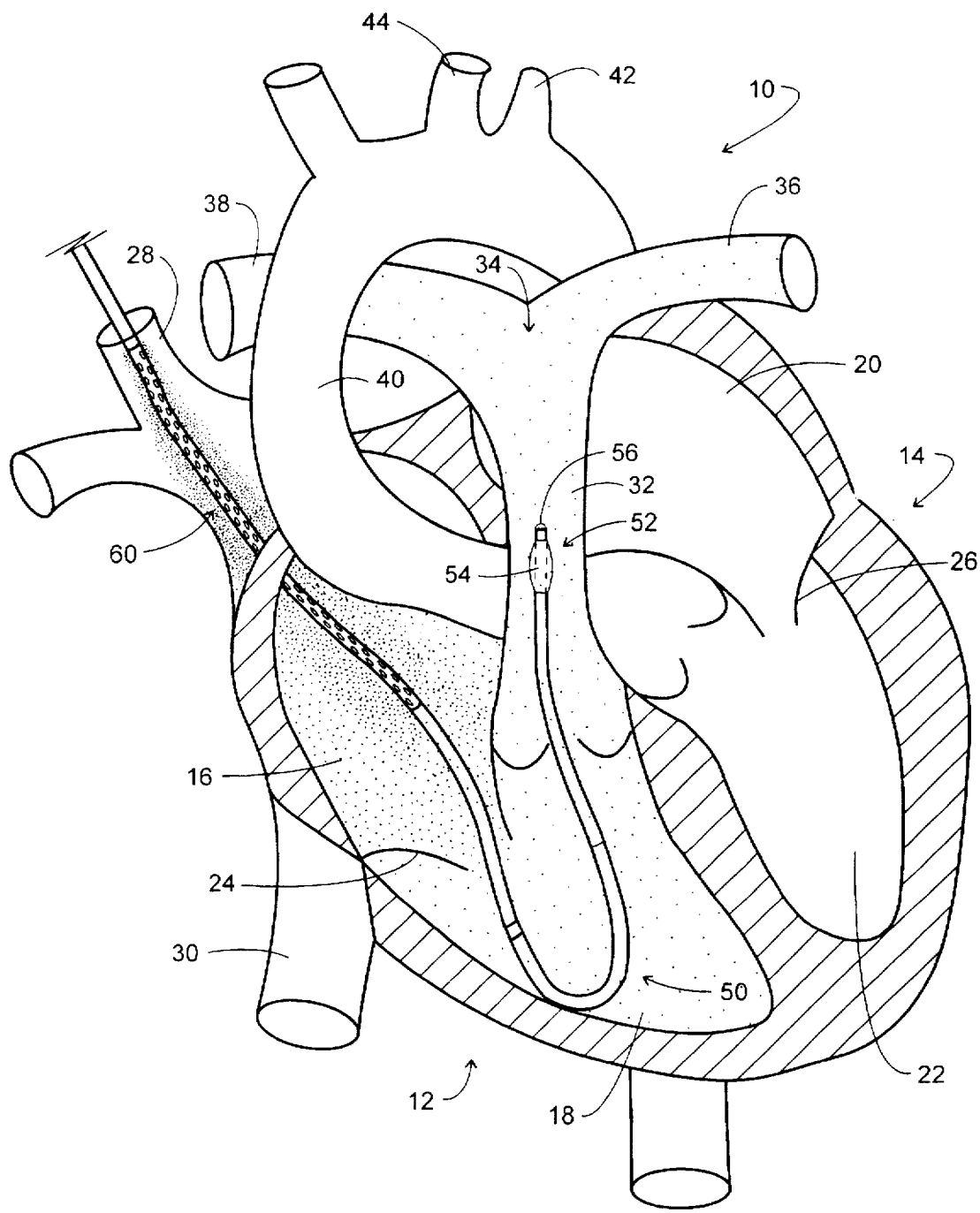
FIG. 1 is a schematic partially sectional view of a heart showing the placement and illustrating the use of a cardiac output measuring catheter according to the invention.

Measurement of cardiac output has been the subject of substantial study and clinical practice since the 1970s. The approach now presented utilizes the technologies evolved from such studies and, in a preferred embodiment, employs the well-established techniques associated with placement of a pulmonary artery, which is the delivery vehicle of choice with current thermodilution techniques. Looking to FIG. 1, a schematic representation of a human heart is identified generally at 10. In general, the heart 10 performs in two stages or sides, having a right side which receives venous-based blood returning from various tissues and vessels of the body and having a somewhat depleted oxygen content. This right side of the heart is seen generally at 12 and functions to pump the oxygen depleted blood arriving from the venous system to the lungs to be oxygenated. Upon being oxygenated, the blood is returned from the lungs and pumped arterially against the vascular resistance of the entire body by the left side of the heart which is represented at 14. The pumping chambers of the heart are represented in FIG. 1 as a right atrium 16 and a right ventricle 18. Correspondingly, the left atrium is shown at 20 and the left ventricle at 22. The right atrioventricular valve is schematically portrayed at 24 and correspondingly, the left atrioventricular (mitral) valve is represented at 26. Looking to input to the right side 12 of the heart 10, the superior vena cava is represented at 28, while the inferior vena cava is represented at 30. The output of the right ventricle is shown extending to the pulmonary artery 32 which, in turn, extends to a bifurcation represented generally at 34 to define a left pulmonary artery 36 and a right pulmonary artery 38. Left ventricle 22 is seen extending to the aorta 40 having an aortic arch from which the left subclavian artery extends as shown at 42 and the left common cortoid artery extends as shown at 44.

A pulmonary artery (PA) catheter adapted to carry out the system and method of the invention is represented generally at 50 at the indwelling location normally encountered for heart monitoring including cardiac output (CO) measurement purposes. In particular, the catheter 50 is located within the heart 10 in a fashion similar to that of the conventional Swan-Ganz flow directed thermodilution catheter. See in this regard, Daily, E., "Techniques in Bedside Hemodynamic Monitoring", C. B. Mosby Co., 1985. Note that the distal end or tip represented generally at 52 and configured with a variety of components including a partially inflated balloon 54 is positioned in the pulmonary artery 32 upstream from the bifurcation 34. At this location, the tip 52 will be immersed in mixed venous blood and from this location all of the blood of the body eventually will flow as it returns to the lungs for oxygenation. Catheters as at 50 conventionally are multi-channeled and formed of a soft or compliant material so as not to unduly interfere with the valve activities of the right side 12 of heart 10. Typically, the devices as at 50 will have a diameter of about 7.5 French (0.09 inch) and a length of about 40 inches. The devices are introduced into the body percutaneously, normally being entered from the subclavian vein and the jugular vein at the shoulder/neck region or alternately from a femoral vein in the leg. Movement into position is achieved as a consequence of blood flow by virtue of the partially inflated balloon 54. Correspondingly, the proper positioning of the tip 52 is confirmed, for example, by the pulmonary blood pressure waveforms developed by utilization of an open-ended fluid filled channel or lumen extending through the catheter 50. This channel is open at the outer tip 56 of the catheter 50. In this regard, insertion of the catheter 50 is stopped when a pressure monitor employed with the blood pressure channel of the catheter exhibits an appropriate pressure profile. When appropriately positioned, the distal end 52 will be located within the pulmonary artery as illustrated. That same tip portion 52 may also contain, for example, a temperature sensor and, in a preferred embodiment, the output and input fiber bundle components of an optical reflectance sensor for determining mixed venous oxygen level as a saturation value. Located upstream in the sense of blood flow a somewhat elongate oxygen infusion component or oxygenator of catheter 50 shown generally at 60 serves to diffuse an oxygen mass into adjacent blood flow at a controlled mass flow rate which diffusion into the bloodstream occurs in the region shown, i.e. at the entrance to and within the right atrium. In general, the diffusing component 60 is configured as a membrane impermeable to blood and permeable to oxygen.

The general procedure for determining cardiac output CO involves, as a preliminary step, a baseline measurement of the oxygen level of mixed venous blood at the pulmonary artery. That data or information having been obtained, then oxygen, a gas biocompatible with the body of the patient, is injected into the blood at the noted measured flow rate through the oxygenator 60 creating a localized increase in the oxygen level in the blood. In FIG. 1, a density of "dots" is used to represent the relative oxygen level in the blood and not bubbles of oxygen. Flowing blood mixes with and dilutes the injected oxygen as the blood flows through the right atrium 16, right ventricle 18, and into the pulmonary artery 32. The greater the mass flow rate of blood, the greater the dilution of the measured level of injected oxygen. This dilution is measured using the blood oxygen level sensor located at the distal end 52, preferably using reflectance oximetry. The terms "mass flow rate" as used herein are meant to include any type of measured gas flow control, e.g. volumetric flow rate where pressure and temperature are known.

Figure 2:
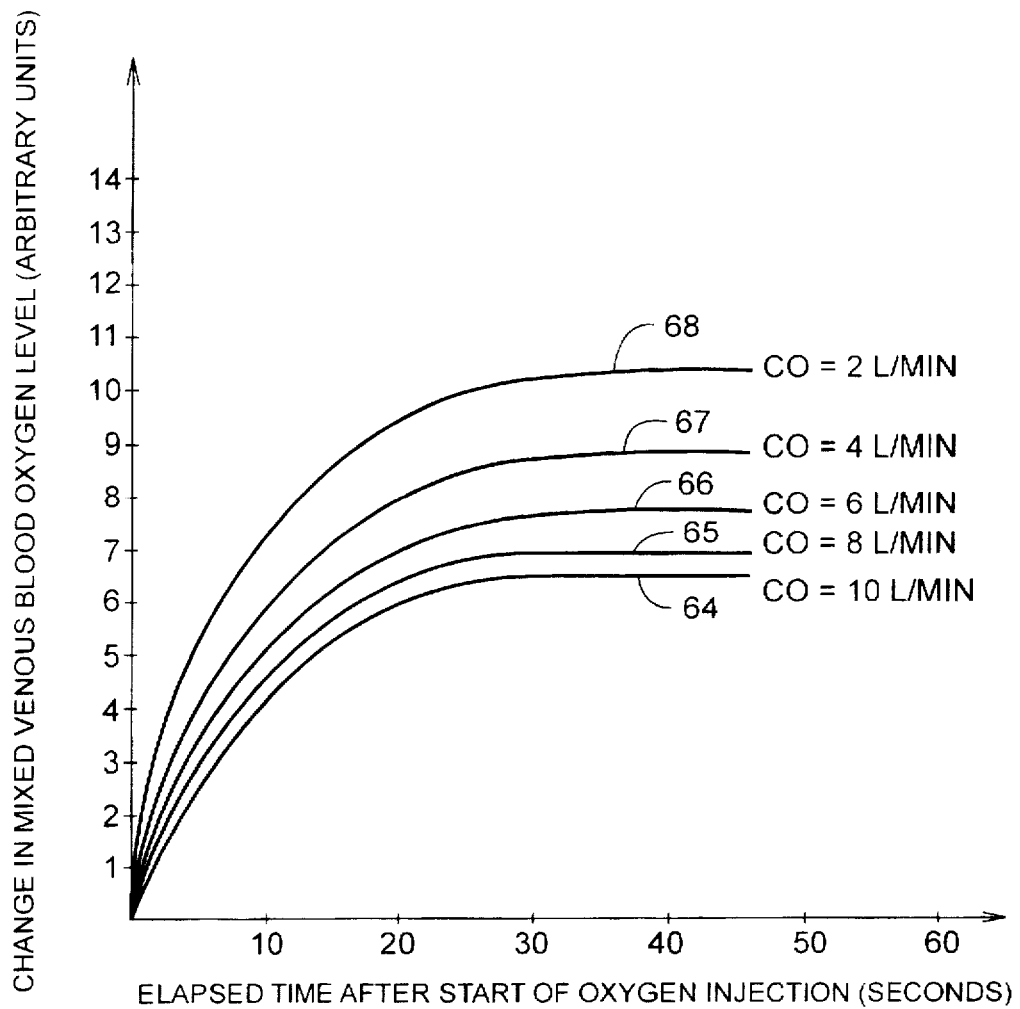
FIG. 2 illustrates a typical response of an oxygen sensor to a fixed amount of injected oxygen based on varying levels of cardiac output.

Looking to FIG. 2, curves 64 through 68 are plotted to reveal values for cardiac output (CO) with respect to elasped time in seconds commencing with the injection of oxygen as further related to the observed change in the mixed venous blood oxygen level. Curves 64-68 correspond, respectively, with cardiac outputs of 10, 8, 6, 4, and 2 liters per minute. It may be observed from the figure that for a given oxygen injection rate, the lower the cardiac output rate, the larger the incremental increase in blood oxygen level. This dependence of the incremental increase in mixed venous blood oxygen level is due to the indicator-dilution effect in which the lower the blood flow rate (i.e. cardiac output), the less a given level of oxygen injection will be dispersed and diluted. In general, the measurement response time of the oxygen sensor employed with the system allows reaching an equilibrium value as shown by the flattened portion of curves 64-68, or some fraction of the end-point equilibrium value within about 10–40 seconds. In effect, the use of a biocompatible gas and attendant data retrieval permits a measurement of CO to be carried out repetitiously over an extended period of time. The repetition or updating rate advantageously may be quite high, thus supplying the intensivist with substantially more current CO data.

Figure 3:
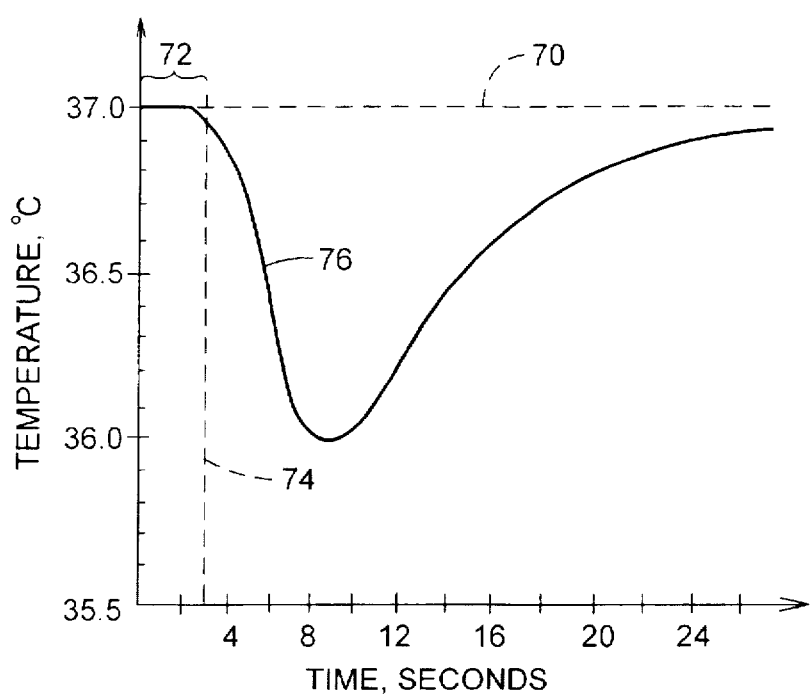
FIG. 3 is a curve illustrating the indicator dilution response of blood temperature to injection of a cold bolus of liquid in accordance with prior art thermodilution techniques.

The characteristic shapes of curves 64-68 as shown in FIG. 2 may be compared with a corresponding temperature/time response encountered in a conventional indicator-dilution approach for developing values of cardiac output, for example, procedures involving a brief injection of a cold saline indicator. In FIG. 3, a mixed venous blood baseline temperature is represented at dashed line 70 having a value, for example, of 37° C. A cold bolus then is injected in the manner discussed over a time interval represented within brackets 72 extending to the time line represented at dashed line 74. During the interval represented at 72, a 10 ml bolus of isotonic saline, for example, at a temperature of 5° C. may be injected at the entrance to the right atrium. Then, as represented by the temperature characteristic curve 76, a thermistor or thermocouple will respond at the region of the pulmonary artery to measure the relatively rapidly changing indicator value for temperature. By contrast, systems of measurement with the present approach may exhibit a relatively slower response time inasmuch as the oxygen indicator may be injected over a lengthier period and at a lower rate, m.

Figure 4:
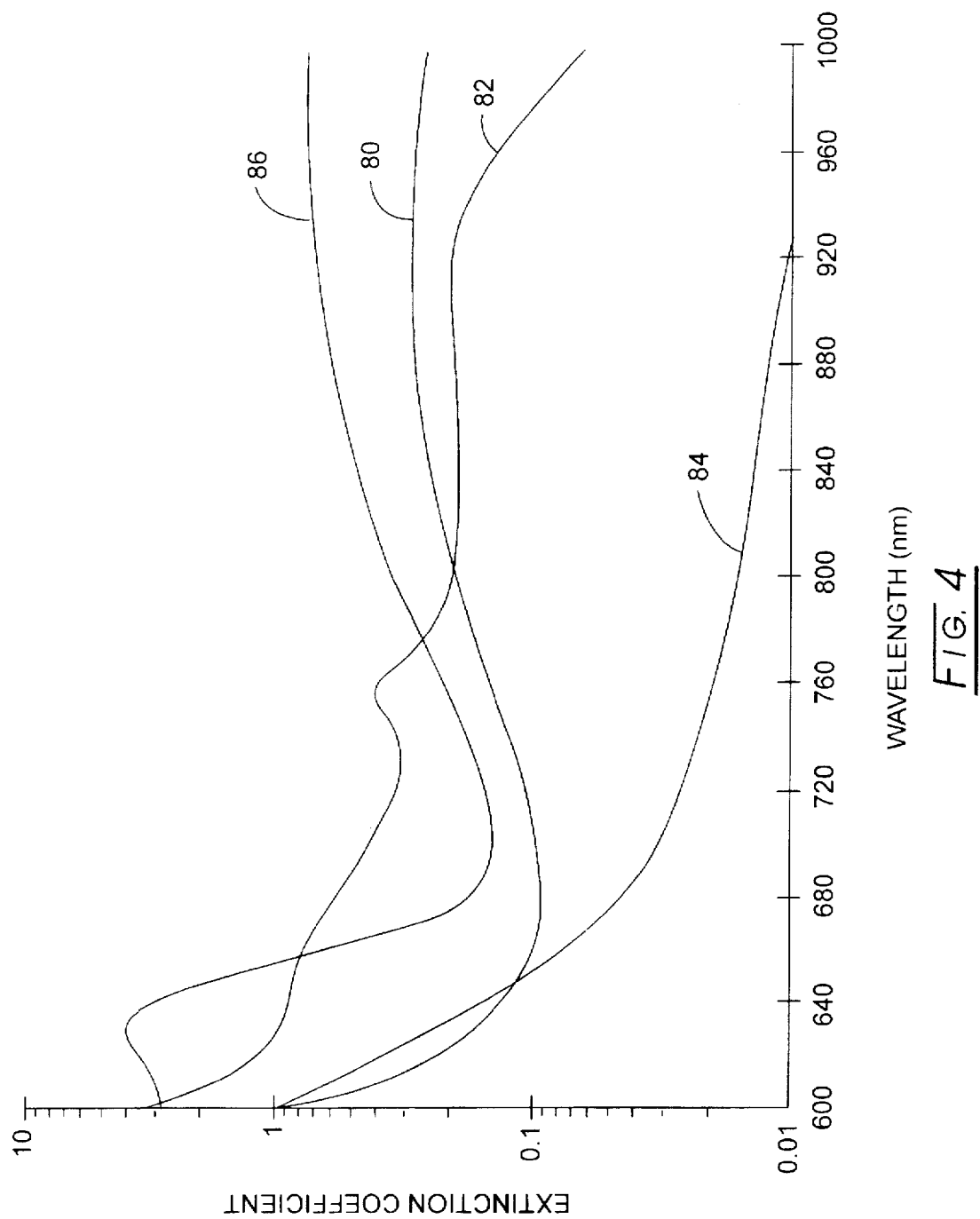
FIG. 4 is a family of curves relating the extinction coefficient of the four hemoglobin species of blood with respect to a sequence of wavelength values.

In the present discussion, the term "blood oxygen level" is meant to include the oxygenated characteristics of one or both of the basic components of the blood, i.e. plasma and hemoglobin. Where it is considered in connection with the plasma component of blood, then it is a dissolved oxygen level. Correspondingly, where the oxygenation is associated with the hemoglobin component of the blood, then it is a bound oxygen function. Generally, the dissolved oxygen levels within the plasma are measurable electrolytically, for example, utilizing a Clark electrode structure. By contrast, bound oxygen levels associated with hemoglobin may be measured utilizing the technique of reflection oximetry. This latter approach is the preferred one in the present invention. Looking momentarily to FIG. 4, hemoglobin extinction curves are revealed relating the four hemoglobin species to wavelength and an extinction coefficient. The two species of hemoglobin which are capable of transporting oxygen are represented in these curves as oxyhemoglobins at curve 80 and reduced hemoglobin as represented at extinction curve 82. Oxyhemoglobin and reduced hemoglobin exist in conjunction with typically minor percentages of two dyshemoglobin species which are dysfunctional to the extent that they do not transport oxygen. Of the two dyshemoglobin species, carboxyhemoglobin, as represented at extinction curve 84, is a hemoglobin component which is bound to carbon monoxide and is thus not available for oxygen transport. Correspondingly, the other dyshemoglobin species is referred to as methemoglobin, a condition or component created by chemical imbalances other than carbon monoxide binding. The methemoglobin species is represented at extinction curve 86. Because of their unavailability for oxygen transport, accommodation is made with respect to the dyshemoglobins represented by extinction curves 84 and 86, although the extent of these components is a relatively lower percentage of total hemoglobin, however, they will be seen to be accommodated for. For further information, see the following publication:

Barker, et al., "Effects of Methemoglobinemia on Pulse Oximetry and Mixed Venous Oximetry", *Aneshtesiology* 70:112–117, 1989.

Figure 5:
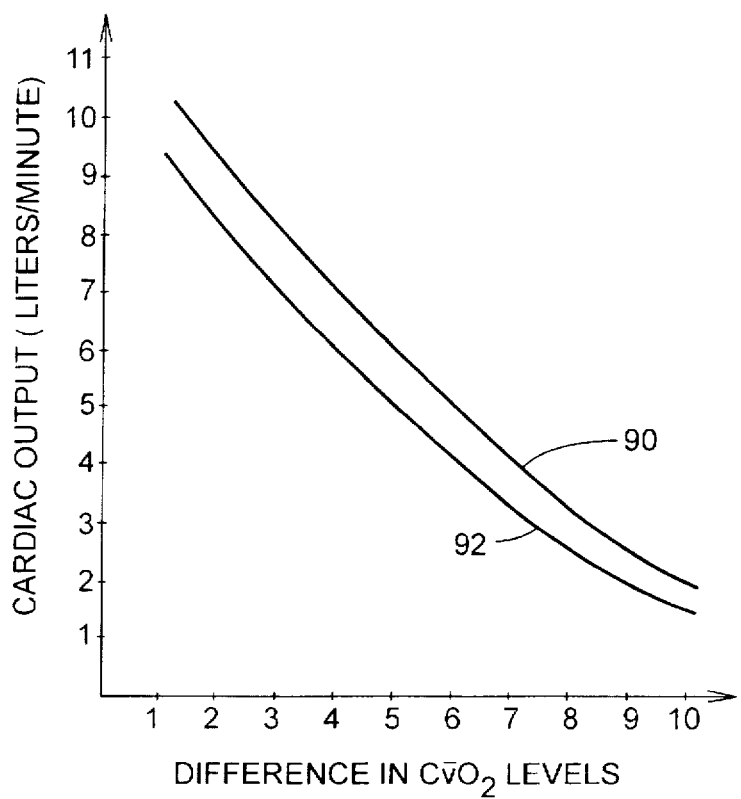
FIG. 5 illustrates the relationship between measured change in oxygen level in blood and cardiac for known oxygen injection rates.

Cardiac output, i.e. volumetric flow rate, is derived empirically as a function of the measured oxygen injection rate, mh and the measured increase in blood oxygen level. These relationships may be plotted. For example, looking to FIG. 5, differences in the mixed venous oxygen content, C $\bar{v}O_2$, for two different rates of oxygen delivery are plotted with respect to cardiac output in liters per minute. Curve 90 plots the different values for $C\bar{v}O_2$ with respect to an oxygen injection rate of a predetermined value typically derived in grams per second. Lower curve 92 is at a lesser oxygen injection rate. As is apparent, a family of such curves will be evolved for a given system. This family of curves may be represented by the following expression:

$$CO = \frac{K * \dot{m}O_2}{10 * [C\bar{v}O_2'(t_i') - C\bar{v}O_2(t_i)]} \quad (1)$$

where CO is cardiac output, in liters per minute, K is a constant, $\dot{m}O_2$ is the rate of oxygen injection in grams per second, $C\bar{v}O_2$ is mixed venous oxygen content in milliliters of oxygen per deciliter of blood at baseline defining time $t_i$ and $C\bar{v}O_2'(t_i')$ is the corresponding mixed venous oxygen content at a subsequent time, $t_i'$, which is the point in time of the second measurement.

In employing the system of the invention, a variety of hemodynamic parameters are considered. These parameters are identified below in conjunction with a sequence of expressions employing them, including the development of the parameters of equation (1) above.

CO=measured cardiac output in liters/minute

BSA=body surface area in m² (calculated based on patient's height and weight)

pH=measured blood pH

CI=cardiac index=CO/BSA (liters/minute m²) (2)

T=measured patient temperature in °C.

$S\bar{v}O_2$=measured mixed venous oxygen saturation in %

$SaO_2$=measured oxygen in arterial plasma (mmHg)

$PaO_2$=dissolved oxygen in arterial plasma (mm Hg)=10 exp [log $P_{50}$+(log $(SaO_2/(1-SaO_2)))/2.7$] (3)

where $P_{50}$=27 mmHg based on normal oxygen dissociation curve $P\bar{v}O_2$=dissolved oxygen in mixed venous plasma (mmHg)=10 exp [log $P_{50}$+(log$(S\bar{v}O_2/(1-S\bar{v}O_2)))/2.7$] (4)

α=solubility coefficient of oxygen (ml[$O_2$]/dl [blood]*mmHg)= 0.0031/[(10 exp (0.024*(38.0−T)))*(10 exp (−0.50(7.40−pH)))] (5)

Hct=measured blood hematocrit in percent

DysHgb=measured blood dyshemoglobin concentration in gm/dl

Hgb=0.3718 (Hct)−1.30−DysHgb (gm/dl) (6)

$Ca_2$=arterial oxygen content (ml[$O_2$]/dl [blood])=[Hgb*1.34*$SaO_2$]+[$PaO_2$*α](7)

where 1.34 has units of ml [$O_2$]/gm[Hgb]

$C\bar{v}O_2$=mixed venous oxygen content (ml [$O_2$]/dl [blood])= [Hgb*1.34*$S\bar{v}O_2$]+[$P\bar{v}O_2$*α] (8)

where 1.34 has units of ml[$O_2$]/gm[Hgb]

{$CaO_2-C\bar{v}O_2$}=arterial-venous oxygen content difference (ml [$O_2$] /dl [blood])

$\dot{D}O_2$=oxygen transport (ml/min)=$CaO_2$*CO*10 (9)

$\dot{V}O_2$=oxygen consumption (ml.min)=($CaO_2-C\bar{v}O_2$)*CO*10 (10)

$\dot{V}O_2$I=oxygen consumption index (ml/min)=$\dot{V}O_2$/BSA (11)

MAP=measured mean arterial pressure in mmHg

MPAP=measured mean pulmonary arterial pressure in mmHg

CVP=measured central venous pressure in mmHg

WP=measured wedge pressure in mmHg

HR=measured heart rate in beats/minute

SVRI=systemic vascular resistance index [(mmHg*m²)/(1/min)]= (MAP−CVP)/CI (12)

PVRI=pulmonary vascular resistance index [(mmHg*m²)/(1/min)] =(MPAP−WP)/CI (13)

SI=stroke index (ml/beat/m²)=CI/(HR*1000) (14)

LVSWI=left ventricular stroke work index (gm·m/m²)=(MAP−WP)*SI*0.0136 (15)

RVSWI=right ventricular stroke work index (gm·m/m²) (MPAP−CVP)*SI*0.0136 (16)

Figure 6:
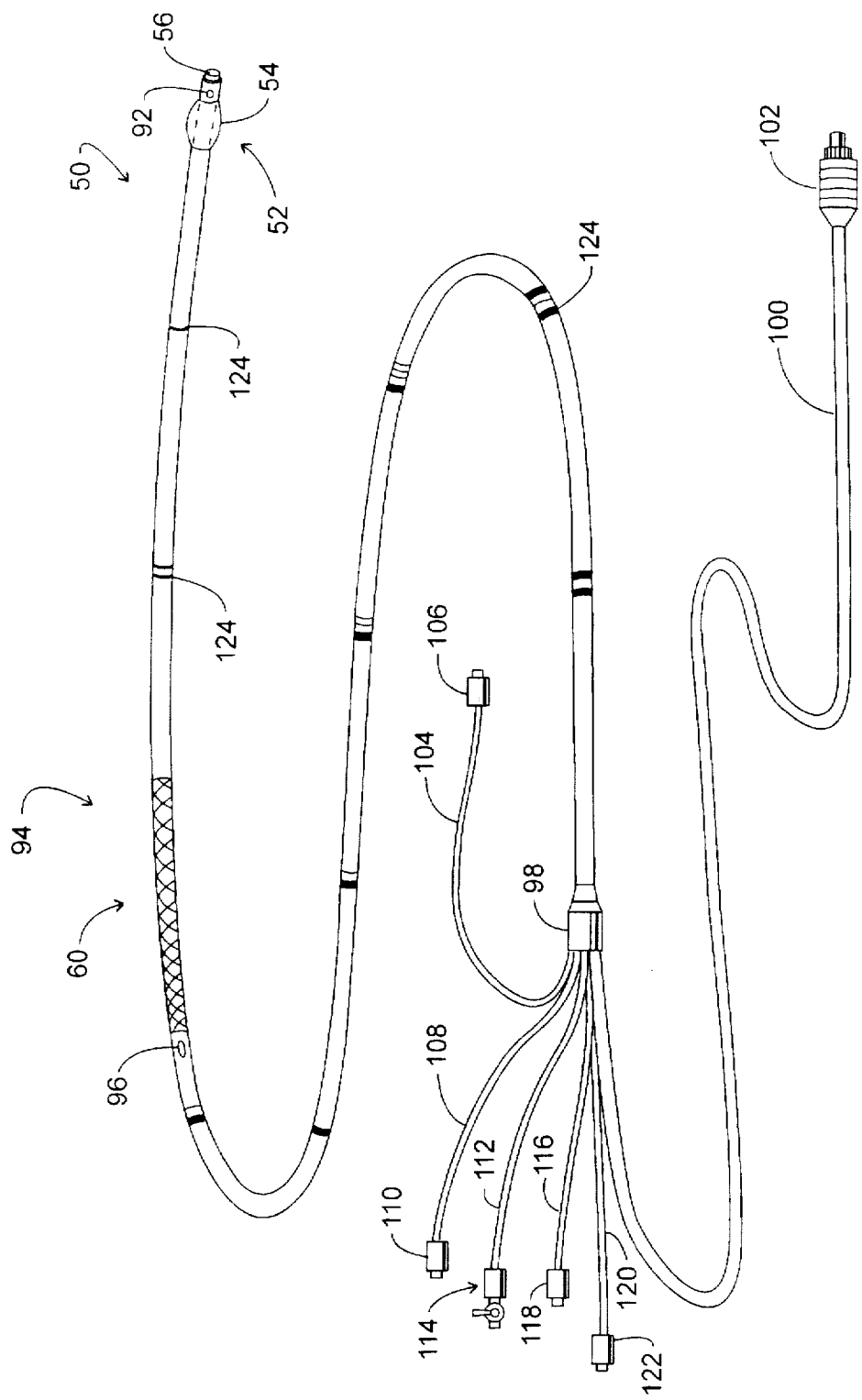
FIG. 6 is a pictorial view of a catheter employed in connection with a preferred embodiment of the invention.

Referring to FIG. 6, the catheter 50 is represented at an enhanced level of detail. The device 50 is generally of a "Swan-Ganz" type, having the noted inflatable balloon 54 at its distal end or tip region 52. The catheter employs a reflectance oximetry approach to determine blood oxygen levels and this reflectance arrangement is implemented through the utilization of fiber optic bundles extending to the tip 56. Also located at the tip 56 is a temperature sensor 92 which may be provided as a thermistor or the like and an open channel or lumen carrying a saline solution which is utilized to monitor blood pressure at the pulmonary artery. Spaced rearwardly from tip region 52 is an indwelling region represented generally at 94 at which location there is positioned an oxygenator or gas infusor earlier described at 60. Typically, the distal portion of oxygenator 60 will be positioned about 30 cm behind the tip 56 and will have a length selected for achieving the rate of oxygen diffusion desired to carry out the dilution indicator procedure. In general, the oxygenator 60 is positioned as discussed in connection with FIG. 1 such that oxygen is diffused into the blood at a location near to and/or within the right atrium of the heart. Adjacent to the oxygenator 60 there is located an auxiliary port 96 which may be used in conventional fashion to introduce medicants into the bloodstream. The port 96 also may be employed to carry out a periodic cardiac output (CO) measurement utilizing the thermaodilution technique with a cold bolus injection.

Catheter 50 terminates at a proximal end or end assembly 98 wherein communication is made between the various channels of it, an oxygen source, and associated control and monitoring features. In this regard, oxygen is supplied at a controlled mass flow rate, mh from a conduit 100 terminating in a connector 102. Transmission and reflection fiber optic bundles extend from end assembly 98 at cable 104 which, in turn, terminates with a connector 106. Communication with the auxiliary port 96 is through tubing 108 which terminates in a fluid connector 110. Balloon 54 is inflated, for example, with carbon dioxide via a gas input at tubing 112 which terminates in a connector and valve assembly 114. The column of liquid channel extending to tip 56 for purposes of blood pressure monitoring extends from end assembly 98 via tubing 116 which, in turn, terminates in a connector 118. Finally, the electrical leads extending to the temperature sensor 92 extend from the end assembly 98 via cable 120 and associated connector 122. Distance markers or length indicators are provided on the catheter as represented, for example, at 124. These markers aid in positioning the device.

Referring to FIGS. 7 and 8, the structure of catheter 50 at the tip region 52 is revealed in sectional fashion. FIG. 7 is a developed view taken along the wedge-shaped section 7—7 shown in FIG. 8, while the latter figure is a section at 8—8 in FIG. 7. In FIG. 7, the tip 56 is revealed as being formed of a polymeric collar 130 which will incorporate cylindrical channels, for example, channel or lumen 132 which extends through the catheter 50 and carries a saline solution for purposes of transmitting blood pressure witnessed at tip 56. The balloon 54 is inflated from an internally disposed port 133 which, in turn, is in gas flow communication with lumen or channel 134. Channel 134 is blocked at collar 130 and receives an inflating gas such as carbon dioxide as earlier described. The two electrical leads 136 and 138 functioning in conjunction with thermistor 92 extend through a channel 140 which also is blocked at tip 56 by the collar 130.

FIG. 8 further reveals the presence of two channels 142 and 144 respectively carrying fiber optic bundles 146 and 148. Additionally, the section reveals an oxygen delivery channel 150 and an auxiliary IV channel 152, the latter two channels will have been blocked rearwardly at the indwelling portion 94 of the catheter 50.

Figure 9:
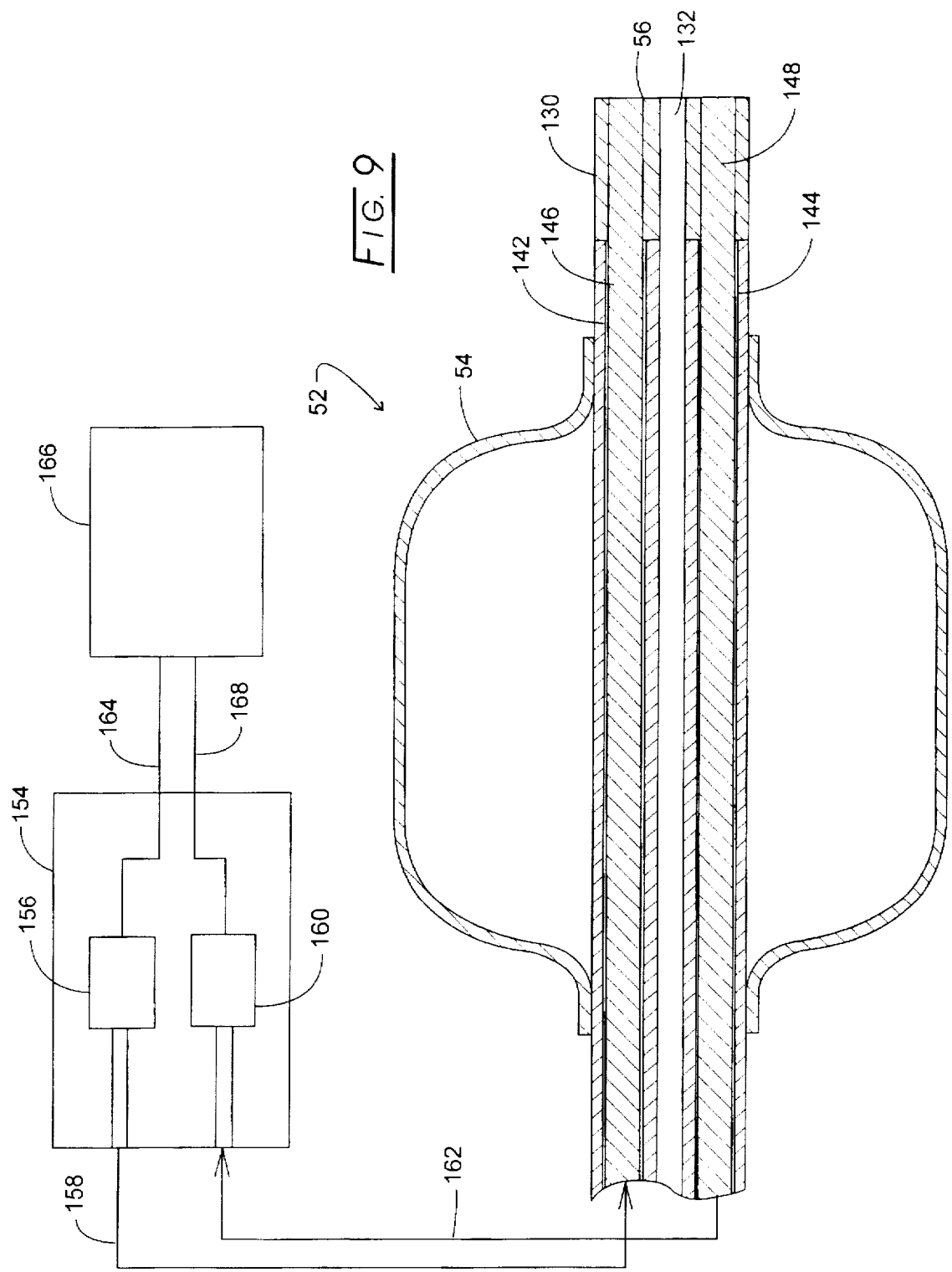
FIG. 9 is a partial sectional view taken through the plane 9—9 shown in FIG. 8.

Referring to FIG. 9, the reflectance oximetry components at the tip region 52 are further illustrated. In this regard, the fiber optical channels 142 and 144 respectively carrying fiber optic bundles 146 and 148 are seen to extend through the polymeric collar 130. As represented in the drawings, these bundles 146 and 148 are connected to a light source and transducer function represented at block 154. This function will include a light source 156 shown associated with fiber optic bundle 146 by arrow 158 and a reflectance responsive transducer is shown at 160 receiving reflectance data from fiber optic bundle 148 as represented at arrow 162. Energization or control over the light source 156 is represented at line 164 extending to a blood oxygen level monitoring system represented at block 166. Similarly, the data developed at transducer 160 is directed to the monitoring function at block 166 as represented at line 168.

Referring to FIGS. 10 and 11, the gas diffusion or oxygenator component 60 of catheter 50 is revealed at an enhanced level of detail.

The figure shows the oxygenator 60 to be formed of a cylindrical membrane 180 which extends about the exterior surface to the body structure 181 to catheter 50 and is spaced therefrom to define an annular oxygen receiving gap 184. The cylindrical membrane 180 is sealed to the outer surface 182 by oppositely disposed generally cylindrically shaped seals 186 and 188. The seals 186 and 188 may be provided, for example, as heat shrinkable tubing or as a suitable adhesive. A controlled oxygen flow is provided at earlier-described channel or lumen 150 which passes from that channel through a port 190 into the gap 184 at a controlled mass rate. As blood passes over the outer surface of the membrane 180, oxygen or suitable biocompatible gas is taken up by it in dissolving fashion with respect to the plasma component and by binding with respect to the component of hemoglobin capable of transporting oxygen, i.e., reduced hemoglobin. Membrane 180 may be provided as an oxygen permeable membrane (e.g., 4 micron thick polyalkylsulfone) which permits the transport of oxygen to the blood passing over the membrane at an oxygen supply gauge pressure of only about 5 to 20 mm Hg. Alternately, a microporous material may be used for the membrane 180. The length of the oxygenator 60 may be from 10 to 100 cm and preferably from about 20 cm to about 40 cm. If a femoral vein is used to introduce the catheter 50, then the length of the oxygen supply portion 60 of the catheter may be as much as 100 cm. (FIG. 10 further reveals that the oxygen carrying channel 150 is plugged or blocked at a plug 192.)

Figure 12:
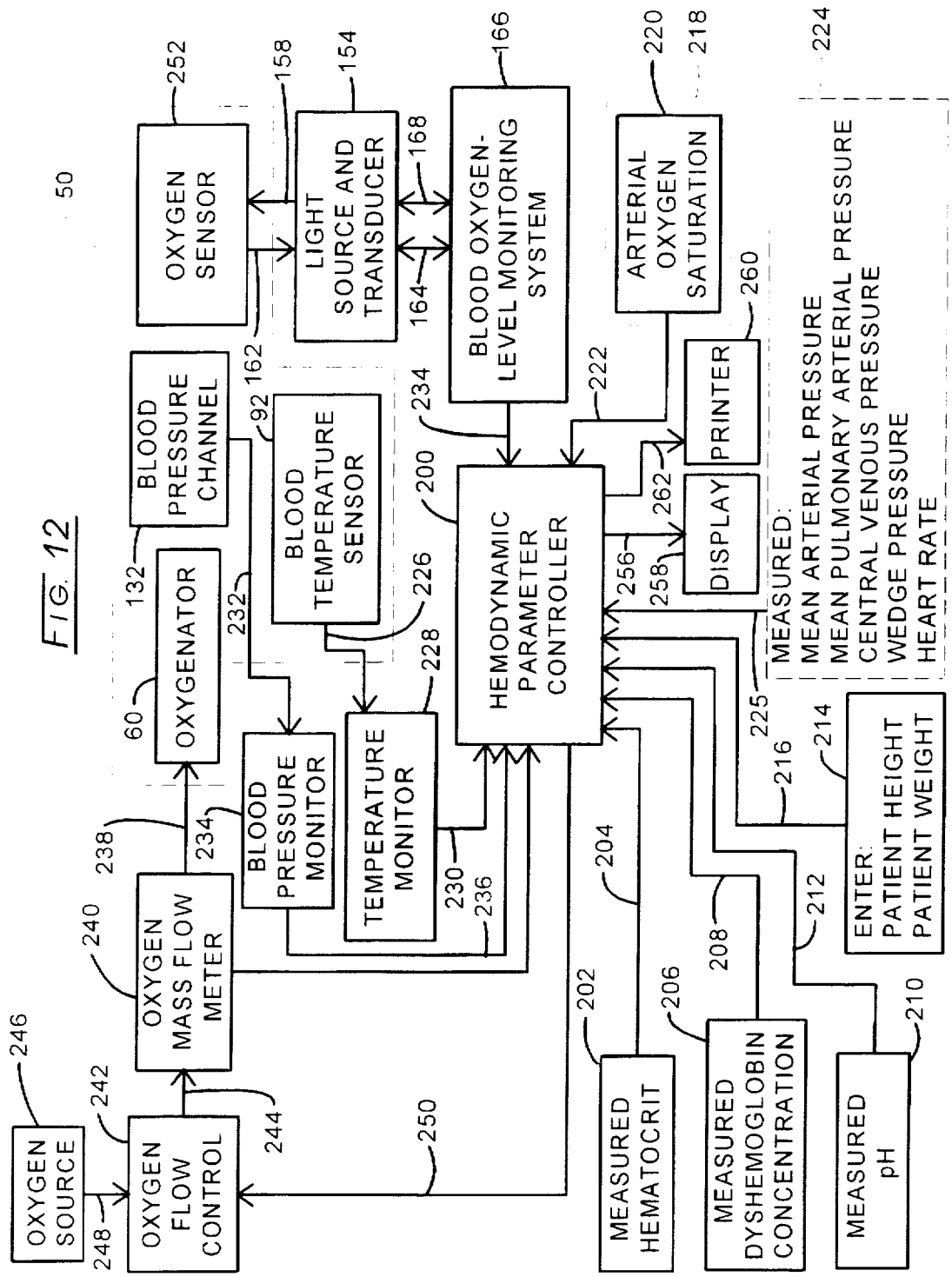
FIG. 12 is a block diagrammatic view of the cardiac output measurement system of the invention.

Referring to FIG. 12, a block diagram of the system within which the catheter 50 performs is represented. This system is operated in conjunction with a microprocessor driven hemodynamic parameter controller. This controller includes the conventional features for achieving control including read only memory (ROM), random access memory (RAM), as well as input/output components including programmable interface adapters which perform in conjunction with input devices such as a keyboard and provide a display function which will include a printer. The controller is represented in the figure at block 200 and, in the course of use of the system, a variety of parameters will be measured and entered into its memory. In this regard, during the course of intensive care, blood samples will be taken periodically from the patient and analyzed. Such analysis will provide, as represented at block 202, a value for hemotocrit (Hct) which may be manually entered into controller 200 as is represented at line 204. Those blood samples additionally will provide a value for dyshemoglobin (DysHgb) concentration as represented at block 206. Entry of this value to controller memory is represented at line 208. pH also is evolved in the course of taking blood samples as represented at block 210, and the entry thereof into controller memory is represented at line 212. The patient's weight and height are entered as represented at block 214 and line 216. This information is utilized in deriving BSA, the body surface area, in $m^2$ in order to ultimately compute cardiac index (CI) as described in conjunction with expression (2) above. Particularly where the data development is associated with dual oximetry, arterial system based information will be desired. For example, another indwelling catheter is represented by dashed boundary 218. Such a device may be employed to derive arterial oxygen saturation as represented at block 220 and arterial oxygen saturation may be monitored continuously using conventional pulse oximetry devices. This parameter ($SaO_2$) is shown to be inputted as represented at line 222. Also measured are the parameters represented within dashed boundary 224 which include mean arterial pressure (MAP); mean pulmonary arterial pressure (MPAP); central venous pressure (CVP); wedge pressure (WP); and heart rate (HR). Of this grouping of measurements, mean arterial pressure (MAP) is measured independently, while the remaining parameters may be measured utilizing the data developed with catheter 50. Entry of the above data into memory is represented at line 225.

The components of cathether 50 are represented within a dashed boundary 50 having the same identifying numeration as given them earlier herein. Such components include a blood temperature sensor earlier described at 92 and represented in block form with the same numeration. The data representing blood temperature is transmitted as represented at line 226 to a temperature monitor represented at block 228 and the resultant data is inputed to the controller 200 as represented at line 230. Similarly, blood pressure data developed from the channel 132 is represented in the figure in block form with that same numerical identification. The output of the blood pressure channel 132 is represented at line 232 as being directed to a blood pressure monitor function represented at block 234, the output from which is directed to controller 200 as represented at line 236.

The oxygenator earlier described at 60 reappears within dashed boundaries 50 in block form and with the same numeration. Oxygen is introduced to the oxygenator 60 as represented at line 238 from an oxygen mass flow meter represented at block 240. Input to the meter 240 is from an oxygen flow control represented at block 242, the output of which is represented at line 244. Flow control 242 performs in conjunction with an oxygen source represented at block 246 and line 248, and is controlled by the controller 200 as represented at line 250. This control provides the variable component of the numerator of expression (1) for cardiac output (CO).

The oxygen sensor function within cathether 50 is represented at block 252 as being associated with lines 158 and 162 as described in conjunction with FIG. 9. Lines carrying those identifying numbers reappear in the instant figure and are seen associated with a light source and transducer function earlier described at block 154 and shown by a block with the same numeration in the instant figure. The output of the light source and transducer are represented by lines 164 and 168 which, as before, extend to a blood oxygen level monitoring system represented at a block 166 in FIG. 9.

which identifying numeration is repeated in the instant figure. The output of the blood oxygen level monitoring system is represented at line 234 extending to the controller 200. Preferably, in carrying out the measurement of the mixed venous oxygen saturation level ($\overline{Sv}O_2$) using oxygen sensor function 252, three wavelengths, $\Lambda_1$, $\Lambda_2$, $\Lambda_3$ are projected and the reflectance thereof are carried by one of the fiber optic bundles as described at 146 and 148. With this reflectance oximetry approach, the difference in extinction coefficient and associated optical reflectance of oxygenated and reduced hemoglobin is used to compute oxygen saturation level of the mixed venous blood. It may be observed in expression (1) above, that the denominator of the equation developing cardiac output, CO, employs the mixed venous oxygen content variable, $\overline{Cv}O_2$. That parameter is computed as represented at expression (8) which is seen to include the dissolved oxygen mixed in venous plasma ($\overline{Pv}O_2$) multiplied by the solubility coefficient, $\alpha$. This latter component of the blood at the pulmonary artery will represent about 3 to 5% of the blood oxygen level at that location. Accordingly, this value may be estimated for computation at controller 200. However, a technique for measuring $\overline{Pv}O_2$ is described later herein.

The parameters derived by controller 200 are directed to two readouts, one a dynamic display or screen as represented at line 256 and block 258, and, for permanent record purposes as well as developing a permanent timeline with time and date data, the information is directed to a printer function as represented at block 260 and line 262.

Data which may be displayed at display 258 is listed in conjunction with FIG. 13 within a block having the same numeration. In this regard, cardiac output (CO) is displayed as is computed in conjunction with expression (1) above. Next, cardiac index (CI) is displayed having been computed in conjunction with expression (2) above. Patient temperature is measurable, for example, utilizing thermistor 92. Mixed venous oxygen content ($\overline{Cv}O_2$) is derived as discussed above in connection with expressions (4), (5), (6) and (8). Arterial oxygen content ($CaO_2$) is derived as described above in connection with expressions (3), (5), (6), and (7). Mixed venous oxygen saturation ($\overline{Sv}O_2$) is measured by the reflectance oximetry of the system as at block 252. Arterial-venous oxygen content difference [$CaO_2$–$\overline{Cv}O_2$] is developed in conjunction with expressions (6) and (7) above. Oxygen transport ($_DO_2$) is developed as described in connection with expressions (9), (1), and (7). Oxygen consumption ($\dot{V}O_2$) is described above in connection with expressions (10), (7), (8), and (1). Oxygen consumption index ($\dot{V}O_2I$) is developed as discussed above in connection with expression (11), which employs body surface area (BSA). Systemic vascular resistance index (SVRI) is developed as discussed above in connection with expression (12). Pulmonary vascular resistance index (PVRI) is developed in conjunction with expression (13) above. Stroke index (SI) is developed in conjunction with expression (14) above. Left ventricular stroke work index (LVSWI) is developed as set forth above in connection with expression (15). Right ventricular stroke work index (RVSWI) is developed in conjunction with expression (16) above.

Figure 14A:
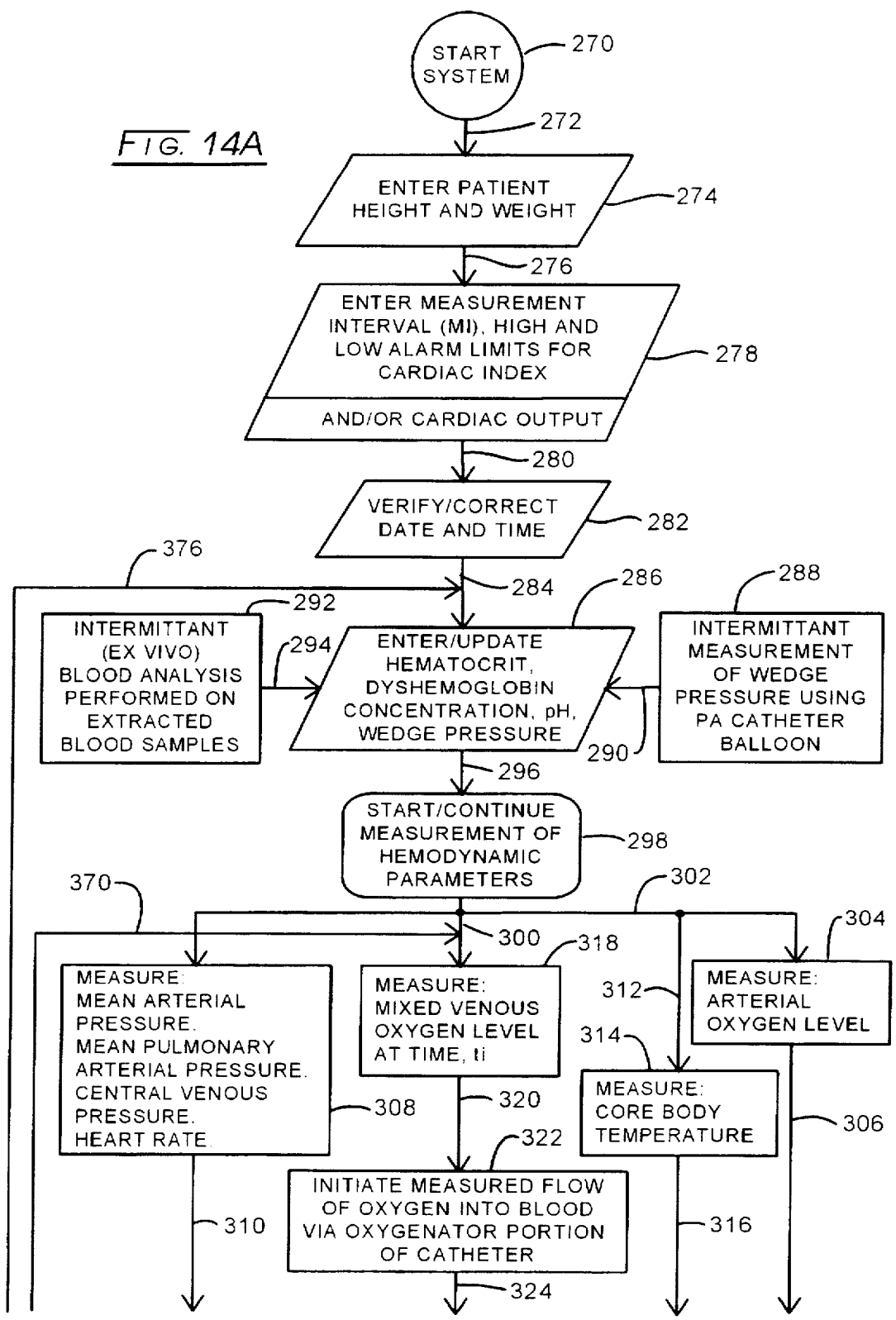
FIGS. 14A and 14B combine to provide a flow chart describing a method for measuring cardiac output employing the system of the invention.
Figure 14B:
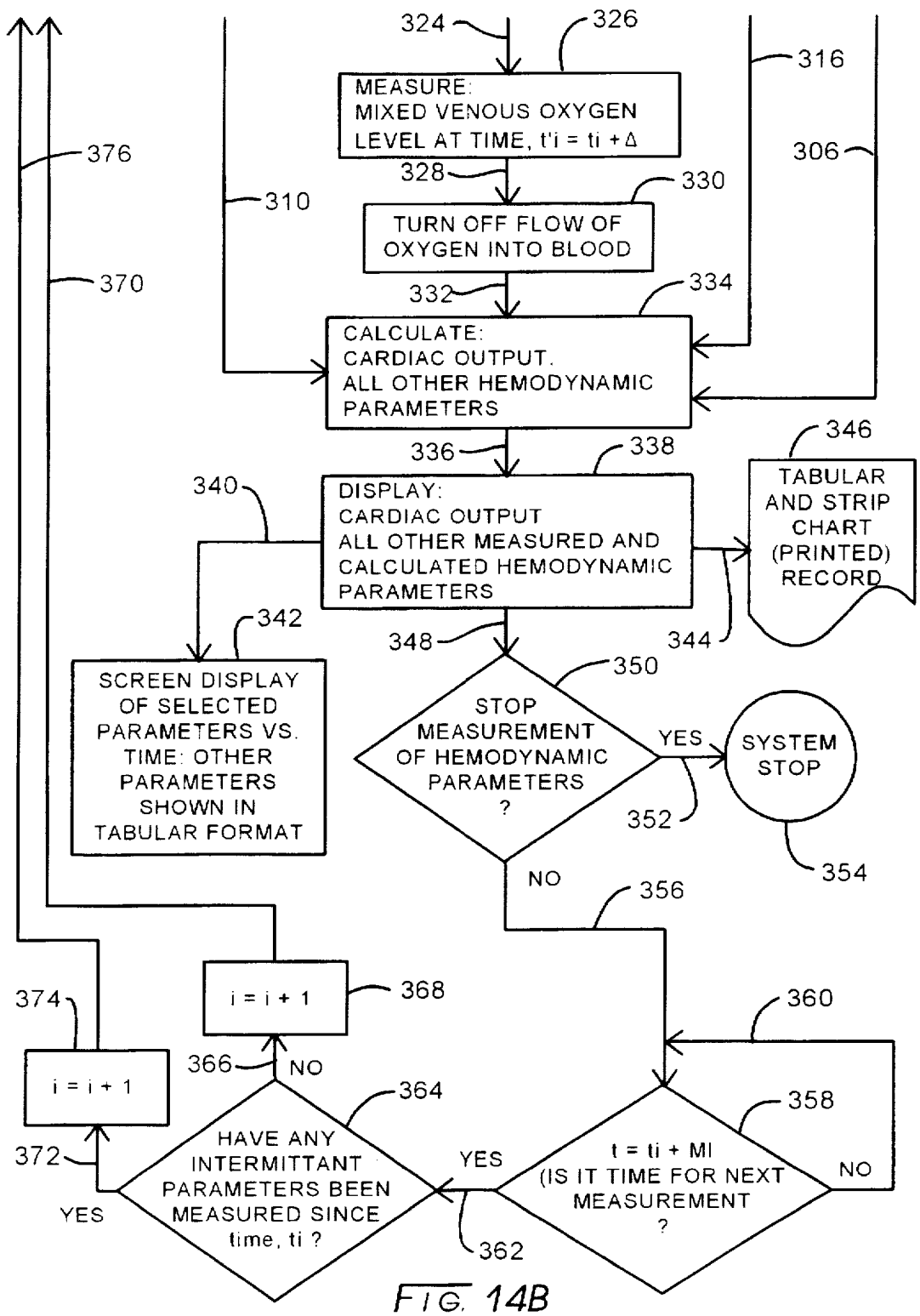

Referring to FIGS. 14A and 14B, a flow chart describing the operation of the system in conjunction with controller 200 is revealed. The system is started as represented at commencing node 270 and, as represented at line 272 and block 274, the initial input is that of entering the height and weight of the patient as discussed earlier at block 214 for the purpose of computing cardiac index (CI) as set forth at expression (2). Next, as represented at line 276 and block 278, the operator elects an interval for carrying out successive measurements, that interval being designated "MI". Additionally, the operator may select high and low alarm limits, for example, for cardiac index values, values falling below the lower limit indicating an inadequate cardiac output. Correspondingly, certain medical intervention may increase the cardiac index above a desired level, thus calling for an alarm condition. The limit, alternately, may be established for cardiac output values. However, the cardiac index is a normalized form of valuation which may be of some benefit for this purpose.

The program then continues as represented at line 280 and block 282 at which point the correct date and time are verified by the operator. This assures that data which is collected is correlated in time and date with manual records and manual interventions which may be carried out.

The program then continues as represented at line 284 and block 286. At block 286, the user manually hematocriters original data or updates data as to the value of hematocrit (Hct), dyshemoglobin concentration (DYS HGB), pH, and wedge pressure (WP). These parameters are developed, in part, in consequence of normal blood sample analysis. Wedge pressure, of course, is measured with the pulmonary artery catheter 50. Block 288 and line 290 show the intermittent measurement of wedge pressure using the pulmonary artery catheter balloon, while block 292 and line 294 show the utilization of intermittent ex vivo blood analysis performed on extracted blood samples. Alternatively, hematocrit may be measured continuously with in-dwelling hematocrit sensing devices, data from which can be supplied to controller 200.

The program then continues as represented at line 296 and block 298 at which position the measurement of hemodynamic parameters is carried out either on a continuing basis or at the start of a monitoring program. Accordingly, as represented at lines 300 and 302, arterial oxygen level may be measured as represented at block 304 and the resultant data will be delivered as represented at line 306. As represented at block 308, mean arterial pressure may be measured. Mean pulmonary arterial pressure may be measured utilizing the blood pressure channel of catheter 50, central venous pressure may be measured, and heart rate may be determined by any of various modalities, including catheter 50, and the data delivered as represented at line 310. Additionally, as represented at line 312 and block 314, core body temperature may be measured and the data delivered as represented at line 316.

Line 300 also is directed to the initial step in carrying out the measurement of cardiac output using the oxygen dilution technique of the invention as represented at block 318. In this regard, the mixed venous oxygen level is measured at a time $t_i$ to provide a baseline value before the introduction of oxygen at the entrance of the right atrium of the heart. This is the first measurement for any iteration of the procedure. Following such measurement, as represented at line 320 and block 322, a measured mass flow of oxygen into the blood via the oxygenator portion 60 of catheter 50 is commenced, and the program continues as represented at line 324.

Referring to FIG. 14B, line 324 reappears in conjunction with block 326, which provides for the measurement of mixed venous oxygen level at time $t'_i=t_i+\Delta$. This $\Delta$ increment of time is selected with respect to the reaching of a blood oxygen level equilibrium as discussed in connection with curves 64–68 in FIG. 2. For more rapid evaluation, the final equilibrium value can be predicted from earlier data in these curves, i.e. one may predict the approach asymtotically. Upon completing the measurement, as represented at line 328 and block 330, the flow of oxygen through oxygenator 60 is turned off and, as represented at line 332 and block 334, cardiac output (CO) is computed as well as all other hemodynamic parameters. In the latter regard, it may be seen that the data earlier developed as represented at line 306 is directed to this function as well as that developed with respect to block 308 and line 310 is provided at this stage. The computed cardiac output and other hemodynamic parameters then, as represented at line 336 and block 338 are displayed as represented at line 340 and block 342. The parameters may be shown in conjunction with a timeline or shown in tabular format. Additionally, as represented at line 344 and symbol 346, a permanent record may be developed as a printed record with a tabulation of parameters as well as a strip chart form of readout.

The program then continues as represented at line 348 to consider the query posed at block 350. That query determines whether or not a stop measurement command has been given. In the even that it has, then, as represented at line 352 and node 354, the system is stopped. In the event that no such stop command has been received, then as represented at line 356 and block 358, the query is posed as to whether the measurement interval as assigned by the user in connection with block 278 has been completed. This interval, MI, always will be at least as long as the minimum interval required to complete a CO measurement. In effect, the measurement interval length is selected to permit the blood oxygen level to return to a physiological baseline value, i.e. that which would be normally present without the additional supplemented oxygen for measurement purposes. In the event of a negative determination, then as represented at line 360 extending to line 356, the system dwells until the interval, MI, has occurred. Where the interval has occurred, then as represented at line 362 and block 364, a determination is made as to whether any intermittent parameters have been measured since the interval commenced for the present measurement, $t_i$. Where no such parameters have been measured, then as represented at line 366 and block 368, the measurement index, i, is changed to i+1, and the program reverts as represented at line 370 which is seen to continue to line 300 in FIG. 14A, at which time, the next measurement of mixed venous blood oxygen level is undertaken as discussed above in connection with block 318.

Where the query posed at block 346 results in an affirmative determination that other intermittent parameters have been measured, then, as represented at line 372 and block 374, the measurement number or index, i, is incremented by 1 and the program reverts as represented at line 376 to line 284 as seen in FIG. 14A, wherein the updated information is entered into the program, and the program continues.

Figure 15:
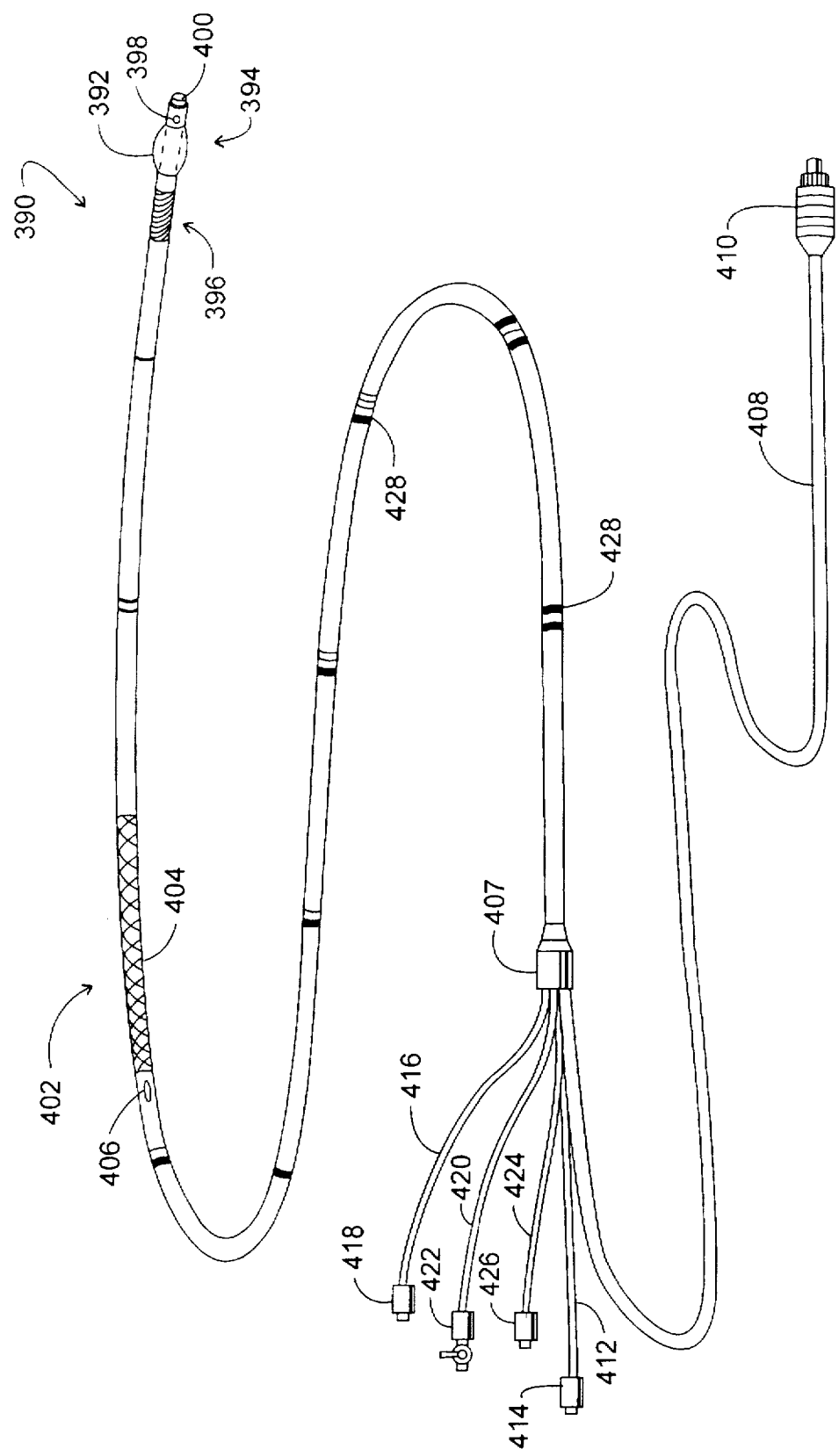
FIG. 15 is a pictorial view of a pulmonary artery catheter for measuring cardiac output in accordance with another embodiment of the invention.

Referring to FIG. 15, a catheter is shown at 390 as being structured in correspondence with another embodiment of the instant invention. Device 390, as before, is generally of a Swan-Ganz type, having an inflatable balloon 392 at its distal end or tip region 394. The cathether employs an electrolytic approach to determine blood oxygen levels, in particular, employing a Clark type electrode which is implemented at the tip region 394 at 396. Also located at the tip region 394 is a temperature sensor 398 which may be provided as a thermistor or the like and an open channel or lumen carrying a saline solution which is utilized to monitor blood pressure at the pulmonary artery. This blood pressure monitoring channel opens at the outward surface 400 of the tip portion 394. Spaced rearwardly from the tip region 394 is an indwelling region represented generally at 402 at which location there is positioned an oxygenator or gas infusor 404. Typically, the distal boundary of oxygenator 404 will be positioned about 20 to 30 cm behind the tip region 394 and will have a length selected for achieving the rate of oxygen diffusion desired to carry out the dilution indicator procedure. In general, the oxygenator 404 is positioned such that oxygen is diffused into the blood at a location near to and/or within the right atrium of the heart as discussed in connection with FIG. 1. Adjacent to the oxygenator 404 there is located an auxiliary port 406 which may be used in conventional fashion to introduce medicants into the bloodstream. The port 406 also may be employed to carry out a periodic cardiac output (CO) measurement utilizing the long recognized thermodilution technique with a cold bolus injection.

Catheter 390 terminates at a proximal end or end assembly 407 wherein communication is made between the various channels of it, an oxygen source, and associated control and monitoring features. In this regard, oxygen is supplied at a controlled gas flow rate, mi, from a conduit 408 terminating in a connector 410. Electrical leads extending from thermistor 398 as well as from the electrode at oxygen sensor 396 extend via a cable 412 to a connector 414. Communication with the auxiliary port 406 is through tubing 416 which terminates in a fluid connector 418. Balloon 392 is inflated, for example, with carbon dioxide via a gas input at tubing 420 which terminates in a connector and valve assembly 422. The column of liquid channel extending to tip end surface 400 for purposes of blood pressure monitoring extends from end assembly 407 via tubing 424 which, in turn, terminates in a connector 426.

Distance markers or length indicia are provided on the catheter as represented, for example, at 428.

Referring to FIGS. 16 and 17, the structure of catheter 390 at the electrode/electrolyte based oxygen sensor region 396 of tip region 394 is revealed. The outer or distal end of the tip region 394 incorporating temperature sensors 398 in end surface 400 is structured identically as the corresponding tip region of catheter 50 as described in conjunction with FIG. 7. Seen in FIG. 16 at the region of the balloon 392 is an inflation/deflation channel 430 which is blocked at a plug 432 to establish an ingress/egress port 434 for carrying out the selective inflation of the balloon 392. Extending along a channel at the center line of the catheter 390 is the blood pressure channel 436, while directly opposite the channel 430 is an electrical lead channel 438 seen in FIG. 17 at this location to retain two electrical leads 440 and 442 extending from the temperature sensor described at 398 in FIG. 15.

FIGS. 16 and 17 reveal the structure of the Clark-type electrode/electrolyte based oxygen sensor 396. The sensor 396 is formed having an outwardly disposed, cylindrically shaped and flexible membrane 450 configured, for example, of polytetrafluoroethylene. Membrane 450 permits an electrolytic transference between the blood within which it is immersed and and interior electrolyte or electrically conducting liquid such as potassium chloride. This electrolyte is shown at 452 as being retained within an annulus shaped cylindrical region, the internal side of which is established by an interior cylindrical wall 454 of the catheter structure 390. The outwardly disposed surface of wall 454 is coated with an electrically conductive material such as gold as shown at 456. This coating 456 extends from a cylindrical end plug 458 (FIG. 16) which establishes one end of the annular shaped electrolyte containing cavity 452. The gold coating 456 terminates at 460 within the cavity 452 and is connected to an electrical lead 462 which is located within the electrical terminal channel 438 in addition to the leads 440 and 442. The second cylindrically shaped electrode of the Clark electrode arrangement is provided as a metallic coating, for example silver, at 464 which is spaced from the electrode deforming coating 456 but remains jointly therewith within the electrolyte containing cavity 452. Cavity 452 terminates within the catheter 390 structure at 466. The second electrode 464 is connected to an electrical lead 468 which additionally is located within the lead containing channel 438. In operation, the electrical leads 462 and 468 are connected across the voltage source of an amperometric oxygen level monitoring system which additionally includes a current sensor. That current sensor measures the current flow in the circuit when such voltage is applied from the voltage source. Typically, the voltage source may be in a range from about 0.6 volts (D.C.) to about 1.0 volts (D.C.) and preferably is retained at about 0.8 volts. The level of current flow resulting from the application of the voltage source to the leads and consequently to the electrodes 456 and 464 will depend upon the level of oxygen dissolved in the plasma components of blood flowing over the arrangement. The resultant current output will be in correspondence with the dissolved oxygen in mixed venous plasma (P $\overline{v}O_2$) as discussed above in connection with expression (4). That expression then may be interpolated empirically in conjunction with the mass flow of oxygen introduced to the system as well as in conjunction with the change from base level values of blood oxygen levels before and after achieving equilibrium following the introduction of oxygen. This has been described in connection with expression (1) above.

Finally, seen in FIG. 17 is the auxiliary channel 470 communicating with port 406 (FIG. 15) and with tubing input 416 and connector 418. Also shown in FIG. 17 is the oxygen delivery channel which will have been blocked off just beyond the location of oxygenator 404.

Referring to FIGS. 18 and 19, the gas diffusion or oxygenator component 404 of catheter 390 is revealed at an enhanced level of detail. It may be observed that the structuring of the oxygenator 404 closely parallels that of oxygenator 60 as described in connection with FIGS. 10 and 11. The instant figures show that the oxygenator 404 is formed of a cylindrical membrane 474 which extends about the exterior surface 476 of catheter 390 and is spaced therefrom to define an annular oxygen receiving gap 478. Cylindrical membrane 474 is sealed to the outer surface 476 by oppositely disposed, generally cylindrically shaped seals 480 and 482. Seals 480 and 482 may be provided, for example, as heat shrinkable tubing or as a suitable adhesive. A controlled oxygen flow is provided at earlier-described channel or lumen 472 which passes from that channel through a port 484 into the gap 476 at a controlled mass flow rate. Note that the oxygen carrying channel 472 is plugged or blocked at a plug 486. As blood passes over the outer surface of membrane 474, oxygen or suitable biocompatible gas is taken up by it in dissolution fashion with respect to the plasma component of the blood and by binding with respect to the component species of hemoglobin capable of transporting oxygen, i.e. oxyhemoglobin reduced hemoglobin. Membrane 474 may be provided as an oxygen permeable membrane, e.g. 4 micron thick polyalkylsulfone which permits the transport of oxgyen to the blood passing over the membrane at an oxygen supply gauge pressure of only about 5 to 20 mm Hg. FIG. 18 further reveals that the oxygen carrying channel 472 is plugged or blocked at a plug 486. Alternately, a microporous material may be used for the membrane 474. The length of the oxygenator 404 may be from 10 to 100 cm and preferably from about 20 cm to about 40 cm. If a femoral vein is used to introduce the catheter 390, then the length of the oxygen supply portion 404 of the catheter may be as much as 100 cm.

Finally, FIG. 19 reveals that the lead carrying channel 438 of the cathether 390, as it extends rearwardly from the electrode/electrolyte based oxygen sensor 336 incorporates four leads, to wit, 440, 442, 462, and 468, which terminate in earlier-described cable 412 and connector 414 (FIG. 15).

Referring to FIG. 20, a block diagram of the system within which the catheter 390 performs is represented. This system is operated in conjunction with a microprocessor driven hemodynamic parameter controller 490. Controller 490 includes the conventional features for achieving control including read only memory (ROM), random access memory (RAM), as well as input/output components including programmable interface adapters or the like which perform in conjunction with input devices such as a keyboard and provide a display function which will include a screen and a printer. Controller 490, and in the course of use of the system, will receive and/or compute a variety of hemodynamic parameters will be entered into its memory. In this regard, during the course of intensive care, blood samples will be taken periodically from the patient and analyzed. Such analysis will provide, as represented at block 492, a value for hemotocrit (Hct) which may be manually entered into the controller 200 as represented at line 494. Such blood samples additionally will provide a value for dyshemoglobin (DysHgb) concentration as represented at block 496. Entry of this value to controller memory is represented at line 498. pH also is evolved in the course of taking blood samples as represented at block 500, and the entry thereof into controller memory is represented at line 502. The patient's weight and height are entered as represented at block 504 and line 506. This information is utilized in deriving BSA, the body surface area in m$^2$ in order to ultimately compute cardiac index (CI) as described in conjunction with expression (2) above. Particularly where the data development is associated with dual oximetry, arterial system based information will be desired. For example, another indwelling catheter is represented by dashed boundary 508. Such a device may be employed to derive arterial oxygen saturation as represented at block 510 therewithin. This parameter (SaO$_2$) is shown to be inputted as represented at line 512. Also measured are the parameters represented within dashed boundary 514 which include mean arterial pressure (MAP); mean pulmonary arterial pressure (MPAP); central venous pressure (CVP); wedge pressure (WP); and heart rate (HR). Of this grouping of measurements, mean arterial pressure (MAP) is measured independently, while the remaining parameters may be measured utilizing the data developed with catheter 390. Entry of the data as represented within dashed boundary 514 into memory is represented at line 516.

The components of catheter 390 are represented within a dashed boundary 390 having the same identifying numeration as given earlier herein. Such components include a blood temperature sensor earlier described at 398 and represented in block form with the same numeration. The data representing blood temperature is transmitted as represented at line 518 to a temperature monitor represented at block 520, and the resultant data is inputted to the controller 490 as represented by line 522. Similarly, blood pressure data developed from the channel 436 is represented in the figure in block form with that same numerical identification. The output of the blood pressure channel 436 is represented at line 524 as being directed to a blood pressure monitor function represented at block 526, the output from which is directed to controller 490 as represented at line 528.

The oxygenator earlier described at 404 reappears within dashed boundary 390 in block form with the same numeration. Oxygen is introduced to the oxygenator 404 as represented at line 530 from an oxygen mass flow meter represented at block 532. Input to the meter 532 is from an oxygen flow control represented at block 534, the output of which is represented at line 536. Flow control 534 performs in conjunction with an oxygen source represented at block 538 and line 540, and is controlled by the controller 490 as represented at line 542.

The electrode/electrolyte based oxygen sensor described earlier at 396 reappears as a block with that numeration. A voltage is applied across the electrodes 464 and 456 of that component and a resultant current flow corresponding with dissolved blood oxygen level is derived by the amperometric oxygen level monitoring system represented at block 544. The resultant data then is directed to the controller 490 as represented at line 546. As before, the information evolved at the controller 490 is provided at a dynamic display screen as represented at block 548 and line 550. Also, a permanent record is developed with time and date information provided by a printer which is represented at block 552, the data input to which is represented at line 554.

The procedure carried out with the instant embodiment essentially follows that described above in connection with the flow chart of FIGS. 14A and 14B. In this regard, hemodynamic parameters are collected as discussed in connection with FIG. 14A and a baseline measurement of mixed venous oxygen level is carried out, for example, at a time, $t_i$. However, for this embodiment, the value derived is dissolved as oxygen in mixed venous plasma or blood, identified above as the parameter, $P\overline{v}O_2(t_i)$. Following the controlled injection of oxygen as discussed in connection with block 322 above, the mixed venous oxygen level is then measured at times $t'_i$. Again, the value will be that of dissolved oxygen in mixed venous plasma. Hemodynamic parameter controller 490 may then compute cardiac output for a given measurement interval in correspondence with the following expression:

$$CO = \frac{W * mO_2}{[P\overline{v}O_2' * t_i') - P\overline{v}O_2(t_i)] * [1 - Hct/100]} \quad (17)$$

where CO is cardiac output, in liters per minute, W is a constant, $mO_2$ is the rate of oxygen injection or mass flow in grams per second, $P\overline{v}O_2$ is the dissolved oxygen in mixed venous blood or plasma in mmHg at baseline defining time, $t_i$, and $P\overline{v}O_2'$ is the corresponding dissolved oxygen in mixed venous plasma in mmHg at subsequent time, $t'_i$, which is the point in time of the second measurement, and Hct is the measured blood hematocrit in percent.

Since certain changes may be made in the above-described system, apparatus, and method without departing from the scope of the invention herein volved, it is intended that all matter contained in the description thereof or shown in the accompanying drawings shall be interpreted as illustrative and not in a limiting sense.

I claim:

1. Apparatus for evaluating the hemodynaric state of the cardiovascular system of the body of a patient, comprising:

a pulmonary artery catheter having a distal end positionable within mixed venous blood at the pulmonary artery of said body and an indwelling region spaced rearwardly therefrom, said catheter extending to a proximal end;

a diffusion channel within said catheter having a gas input connectable with a controlled source of gas biocompatible with said body and extending to an infusion component located at said indwelling region and configured for infusing said gas into the bloodstream of said body; and a gas sensor component mounted upon said catheter at said distal end and having an output corresponding with a level of said biocompatible gas within said mixed venous blood.

2. The apparatus of claim 1 in which:

said infusion component is a membrane impermeable to blood and permeable to oxygen; and said source of gas is a source of oxygen.

3. The apparatus of claim 1 in which:

said source of gas is a source of oxygen;

said gas sensor component includes:

a transmission fiber optic component within said catheter in optical communication with said mixed venous blood at said pulmonary artery when said distal end is positioned thereat; and a reflectance fiber optic component within said catheter in optical communication with said mixed venous blood and responsive to reflection therefrom induced by the transmission through said transmission fiber optic component of light at predetermined wavelengths to provide reflectance oximetry data at said proximal end as said output.

4. The apparatus of claim 3 in which:

said transmission fiber optic component is located at a light transmission channel within said catheter extending between said proximal end and said distal end;

said reflection fiber optic component is located at a reflection transmission channel within said catheter extending between said proximal end and said distal end.

5. The apparatus of claim 1 including:

a temperature sensor mounted upon said catheter at said distal end and having a temperature value output at said proximal end corresponding with the value of temperature of mixed venous blood at said pulmonary artery when said distal end is positioned thereat;

an auxiliary port within said catheter at said indwelling region; and an auxiliary channel within said catheter extending in fluid transfer communication from said auxiliary port to said proximal end for delivering fluid through said auxiliary port.

6. The apparatus of claim 1 in which said catheter includes an incompressible fluid containing blood pressure measuring channel extending between said distal and proximal ends in open communication with mixed venous blood at said pulmonary artery when said distal end is positioned thereat.

7. The apparatus of claim 1 in which:

said source of gas is a source of oxygen; and said infusion component is an oxygenator.

8. The apparatus of claim 7 in which:

said diffusion channel extends in gas flow communication to a gas outlet port formed within a wall of said catheter at said indwelling region; and said oxygenator comprises a cylindrical membrane mounted over said gas outlet port and spaced from said wall to define an oxygen receiving gap, said membrane being impermeable to blood and permeable to oxygen.

9. The method for evaluating the hemodynamic state of the cardiovascular system of the body of a patient, comprising the steps of:

(a) providing a pulmonary artery catheter having a proximal end, a distal end and an indwelling region spaced rearwardly therefrom, a diffusion channel within said catheter having a gas input connectable with a source of gas biocompatible with said body and extending to an infusion component located at said indwelling region and configured for infusably conveying said gas into the bloodstream of said body, and a gas sensor component mounted upon said catheter at said distal end and having an output corresponding with a level of said biocompatible gas within blood at the location of said sensor;

(b) positioning said pulmonary artery catheter within the bloodstream of said body, locating said sensor component at the pulmonary artery and said infusion component upstream therefrom;

(c) deriving said output from said gas sensor to provide a baseline value corresponding with a level of said biocompatible gas within mixed venous blood;

(d) delivering said gas from said source into said diffusion channel at a predetermined mass flow rate;

(e) deriving said output from said gas sensor; and (f) deriving a value for the cardiac output of the heart of said body by correlating said baseline value, said predetermined mass flow rate and said output derived in step (e).

10. The method of claim 9 in which:

said catheter is connectable with a source of oxygen as said gas;

said infusion component is provided as an oxygenator; and said output from said sensor is derived in correspondence with the blood oxygen level of said mixed venous blood.

11. The method of claim 10 in which each said output from said sensor is derived as a level of mixed venous oxygen saturation.

12. The method of claim 11 in which:

said step (a) includes the step of:

(a1) determining the hemoglobin level of said bloodstream in the absence of dyshemoglobin;

said step (c) including the steps of:

(c1) determining the level of dissolved oxygen in said mixed venous blood;

(c2) deriving a baseline value for mixed venous oxygen content by correlating said level of mixed venous oxygen saturation with said hemoglobin level and with said level of dissolved oxygen in said mixed venous blood;

said step (e) including the step of:

(e1) deriving a subsequent value for mixed venous oxygen content by correlating said level of mixed venous oxygen saturation with said hemoglobin level and with said level of dissolved oxygen in said mixed venous blood; and, said step (f) includes the step of:

(f1) correlating said baseline value and said output derived in step (e1) by determining the difference between said subsequent value and said baseline value for mixed venous oxygen content.

13. The method of claim 12 in which said step (a1) includes the steps of:

(a1i) determining blood hemotocrit (Hct) in percent, (a1ii) determining blood dyshemoglobin (DysHgb) concentration;

(a1iii) determining said hemoglobin level (Hgb) in correspondence with the expression:

$$Hgb = 0.3718 \, (Hct) \times 1.30 - DysHgb.$$

14. The method of claim 13 in which said step (c1) is carried out in correspondence with the expression:

$$PvO_2 = 10 \exp |\log P_{50} + (\log (\overline{Sv}O_2/1 - \overline{Sv}O_2))/2.7|$$

where $PvO_2$ is the value of dissolved oxygen in mixed venous blood, and $\overline{Sv}O_2$ is mixed venous oxygen saturation.

15. The method of claim 14 in which said steps (c2) and (e1) are carried out in correspondence with the expression:

$$\overline{Cv}O_2 = |Hgb * 1.34 * \overline{Sv}O_2| + |PvO_2 * \alpha|$$

where $\overline{Cv}O_2$ is mixed venous oxygen content, Hgb is said hemoglobin level, $\overline{Sv}O_2$ is said mixed venous oxygen saturation, $PvO_2$ is said value of dissolved oxygen in mixed venous blood, and $\alpha$ is a solubility coefficient of oxygen.

16. The method of claim 15 in which said step (f) is carried out in correspondence with the expression:

$$CO = \frac{K * \dot{m}O_2}{10 * |\overline{Cv}O'_2(t_i') - \overline{Cv}O_2(t_i)|}$$

where CO is cardiac output, K is a constant, $\dot{m}O_2$ is the value of mass flow rate of oxygen, $\overline{Cv}O_2(t_i)$ is said baseline value for mixed venous oxygen content and $\overline{Cv}O'_2(t_i')$ is said subsequent value for mixed venous oxygen content.

17. The method of claim 10 in which said output from said sensor is derived by blood reflectance oximetry.

18. The method of claim 10 in which said output from said sensor is derived as the level of dissolved oxygen in said mixed venous blood.

19. The method of claim 18 in which said output from said sensor is derived electrolytically.

20. The method of claim 18 in which said step (f) includes the step of:

(f1) determining blood hematocrit (Hct) in percent; and said step (f) is carried out in correspondence with the expression:

$$CO = \frac{W * \dot{m}O_2}{[\overline{Pv}O_2' * t_i') - \overline{Pv}O_2(t_i)] * [1 - Hct/100]}$$

where CO is cardiac output, W is a constant, $\dot{m}O_2$ is the value of mass flow rate of oxygen, $\overline{Pv}O_2(t_i)$ is the dissolved oxygen in mixed venous blood corresponding with said baseline value and $\overline{Pv}O_2'(t_i)'$ is dissolved oxygen in mixed venous blood corresponding with said output of step (e), and Hct is said blood hematocrit.

21. A system for evaluating the hemodynamic state of the cardiovascular system of the body of a patient comprising:

a source of gas biocompatible with said body;

gas flow control apparatus coupled with said source of gas and controllable to provide a select mass flow rate of said gas at a gas output;

a pulmonary artery catheter having a distal end positionable within mixed venous blood at the pulmonary artery of said body and an indwelling region located rearwardly therefrom, said catheter extending to a proximal end;

a blood gas level sensor component mounted with said catheter at said distal end and controllable to provide a sensor output at said proximal end corresponding with a blood gas level within said mixed venous blood;

a diffusion channel within said catheter having an input adjacent said proximal end connectable in gas flow communication with said gas output and having an infusion component located at said indwelling region for diffusing said gas with blood flowing adjacent thereto;

a controller for controlling said gas flow control apparatus and said gas level sensor, and responsive to said sensor output for deriving a first output signal in correspondence therewith representing a value of cardiac output; and a display responsive to said first output signal for displaying said value of cardiac output.

22. The system of claim 21 in which:

said source of gas is a source of oxygen;

said controller effects control of said sensor to derive a baseline blood oxygen level of said mixed venous blood and submits said base line blood oxygen level to a memory, then said controller effects control of said gas flow control apparatus to effect a select mass flow rate delivery of oxygen through said diffusion channel while simultaneously controlling said sensor to derive a subsequent value for blood oxygen level, and is responsive to correlate said baseline blood oxygen level, said select mass flow rate and said subsequent value for blood oxygen level to derive said first output signal representing a value of cardiac output.

23. The system of claim 22 in which said controller includes a timer and is responsive to a select measurement interval time value for carrying out derivations of said first output signal representing cardiac output for each select measurement interval of a succession of such intervals.

24. The system of claim 22 in which said blood gas level sensor is configured to derive said blood gas level sensor output by reflectance oximetry as a value for mixed venous blood oxygen saturation.

25. The system of claim 24 in which said controller is responsive to input values for hematocrit and dyshemoglobin concentration of the blood of said patient retained in said memory and to correlate these input values with said value for mixed venous blood oxygen saturation to derive said first output signal representing cardiac output.

26. The system of claim 25 in which said controller is responsive to inputted values representing the height and weight of said body retained in said memory to derive a value for body surface area therefrom, and is responsive to said value of cardiac output and said value for body surface area to derive a third output signal representing a value of cardiac index; and said display is responsive to said third output signal for displaying said derived value representing cardiac index.

27. The system of claim 26 in which said controller is responsive to an inputted lower threshold limit value for cardiac index retained in said memory and to said derived value of cardiac index to derive a fourth output signal when said derived value of cardiac index is below said threshold limit value for cardiac index; and said display is responsive to said fourth output signal for displaying alarm information with respect to said derived value of cardiac index.

28. The system of claim 27 in which said controller is responsive to an inputted upper limit value for cardiac index retained in said memory and to said derived value of cardiac index to derive a fifth output signal when said derived value of cardiac index is above said upper limit value for cardiac index; and said display is responsive to said fifth output signal for displaying alarm information with respect to said derived value of cardiac index.

29. The system of claim 26 in which said controller is responsive to an inputted value of heart rate of said patient retained in said memory and to said value of cardiac index to derive an eleventh output signal representing a value of stroke index; and said display is responsive to said eleventh output signal for displaying said value of stroke index.

30. The system of claim 26 in which said controller is responsive to inputted values for mean pulmonary arterial pressure and wedge pressure, retained in said memory and is responsive to said value of cardiac index to derive a thirteenth output signal representing a value of pulmonary vascular resistance index; and said display is responsive to said thirteenth output signal for displaying said value of pulmonary vascular resistance index.

31. The system of claim 24 in which said controller is responsive to input values for hematocrit, dyshemoglobin concentration, dissolved oxygen in mixed venous plasma and a solubility coefficient of oxygen retained in said memory and to correlate these input values with said value for mixed venous blood oxygen saturation to derive values for mixed venous oxygen content and said first output signal representing cardiac output.

32. The system of claim 31 in which said controller is responsive to said derived values for mixed venous oxygen content corresponding with said baseline blood oxygen level to derive a second output signal representing a value of mixed venous oxygen content; and said display is responsive to said second output signal for displaying said value of mixed venous oxygen content.

33. The system of claim 32 in which said controller is responsive to inputted values for mean arterial pressure and central venous pressure retained in said memory and is responsive to said value of cardiac index to derive a twelfth output signal representing a value of systemic vascular resistance index; and said display is responsive to said twelfth output signal for displaying said value of systemic vascular resistance index.

34. The system of claim 31 in which said controller is responsive to an inputted value for arterial oxygen content retained in said memory and is further responsive to a said derived value for mixed venous oxygen content corresponding with said baseline oxygen level to derive a sixth output signal for the value of arterial venous oxygen content difference; and said display is responsive to said sixth output signal for displaying said value of arterial-venous oxygen content difference.

35. The system of claim 31 in which said controller is responsive to an inputted value for arterial oxygen content retained in said memory and is further responsive to said derived value for mixed venous oxygen content corresponding with said baseline oxygen level and to said value of cardiac output to derive a ninth output signal for the value of oxygen consumption; and said display is responsive to said ninth output signal for displaying said value of oxygen consumption.

36. The system of claim 35 in which said controller is responsive to inputted values representing the length and weight of said body retained in said memory to derive a value for body surface area therefrom and is responsive to said value of oxygen consumption and to said value for body surface area to derive a tenth output signal representing a value of oxygen consumption index; and said display is responsive to said tenth output signal for displaying said value of oxygen consumption index.

37. The system of claim 24 in which said controller is responsive to said value for mixed venous blood oxygen saturation corresponding with said baseline blood oxygen level to derive a seventh output signal for the value of mixed venous blood oxygen saturation; and said display is responsive to said seventh output signal for displaying said value of mixed venous blood oxygen saturation.

38. The system of claim 24 in which said controller is responsive to an inputted value for arterial content retained in said memory and is further responsive to derived values of cardiac output to derive an eighth output signal for the value of oxygen transport; and said display is responsive to said eighth output signal for displaying said value of oxygen transport.

39. The system of claim 22 in which said blood gas level sensor is configured to derive said blood gas level sensor output electrolytically as a value for dissolved oxygen in mixed venous plasma.

40. The system of claim 22 in which said controller is responsive to an inputted lower threshold limit value for cardiac output retained in said memory and to said derived value of cardiac output to derive a 14th output signal when said derived value of cardiac output is below said threshold limit value for cardiac output; and said display is responsive to said 14th output signal for displaying alarm information with respect to said derived value of cardiac output.

41. The system of claim 22 in which said controller is responsive to an inputted upper limit value for cardiac output retained in said memory and to said derived value of cardiac output to derive a 15th output signal when said derived value for cardiac output is above said upper limit value for cardiac output; and said display is responsive to said 15th output signal for displaying alarm information with respect to said derived value of cardiac output.

* * * * *